(12) United States Patent
Louvet et al.

(10) Patent No.: US 7,960,176 B2
(45) Date of Patent: Jun. 14, 2011

(54) METHOD AND DEVICE FOR DETERMINING IF A PRODUCT IS IN CONDITION FOR USE OR CONSUMPTION

(75) Inventors: Olivier Louvet, Strasbourg (FR); Dominique Thuault, Pleuven (FR); Renaud Vaillant, Gentilly (FR)

(73) Assignee: Cryolog SA, Boulogne (FR)

( * ) Notice: Subject to any disclaimer, the term of this patent is extended or adjusted under 35 U.S.C. 154(b) by 920 days.

(21) Appl. No.: 10/572,327

(22) PCT Filed: Sep. 17, 2004

(86) PCT No.: PCT/EP2004/052237
§ 371 (c)(1),
(2), (4) Date: Mar. 21, 2007

(87) PCT Pub. No.: WO03/025529
PCT Pub. Date: Mar. 27, 2003

(65) Prior Publication Data
US 2007/0275467 A1 Nov. 29, 2007

(30) Foreign Application Priority Data

Sep. 17, 2003 (FR) .................................... 03 50556
Feb. 3, 2004 (FR) .................................... 04 50200

(51) Int. Cl.
*G01N 33/02* (2006.01)
(52) U.S. Cl. ................ 436/1; 436/2; 436/164; 422/400; 422/430; 426/87; 426/232
(58) Field of Classification Search .................. 422/400, 422/430; 436/1, 2, 164; 426/87, 232
See application file for complete search history.

(56) References Cited

U.S. PATENT DOCUMENTS

| 3,616,255 | A | * | 10/1971 | Nakagawa ....................... 435/14 |
| 2002/0031796 | A1 | * | 3/2002 | Townsend et al. ............... 435/34 |
| 2010/0196636 | A1 | * | 8/2010 | Gorski et al. ................ 428/35.7 |

FOREIGN PATENT DOCUMENTS

| EP | 0497459 | 8/1992 |
| WO | WO 92/14998 A | 9/1992 |
| WO | WO 03/025529 A | 3/2003 |

OTHER PUBLICATIONS

Barakat et al., Isolation and Characterization of *Carnobacterium*, *Lactococcus*, and *Enterococcus* spp. From Cooked, Modified Atmosphere Packaged, Refrigerated, Poultry Meat, International Journal of Food Microbiology 62 (2000), pp. 83-94. Hamasaki et al., Behavior of Psychrotrophic Lactic Acid Bacteria Isolated From Spoiling Cooked Meat Products, Applied and Environmental Microbiology, Jun. 2003, vol. 69, No. 6 pp. 3668-3671.
Samelis et al., The Microbial Association of Greek Taverna Sausage Stored at 4 and 10° C in Air, Vacuum or 100% Carbon Dioxide, and Its Spoilage Potential, Journal of Applied Microbiology 2000, 88, pp. 58-68.

* cited by examiner

*Primary Examiner* — Lyle A Alexander
(74) *Attorney, Agent, or Firm* — RatnerPrestia

(57) ABSTRACT

A method and device for determining whether a product is in condition to be used or consumed, this product being intended to be preserved under temperature conditions and for a period of time which limit its degradation includes an indicator combined with the product, to provide a signal indicating that the product can be used or consumed, and then, after the expiration of a preservation period of time, a signal indicating a change in the condition of possible use or consumption of the product. The period of time depends on the preservation conditions of the product. The indicator provides information enabling the product to be used or consumed for a longer period of time if the product has been preserved under conditions better than recommended conditions or for a shorter period of time if the product has been preserved under conditions worse than recommended conditions.

41 Claims, 11 Drawing Sheets

METHOD AND DEVICE FOR DETERMINING IF A PRODUCT IS IN CONDITION FOR USE OR CONSUMPTION

FIELD OF THE INVENTION

The present invention pertains to a method and an indicator for determining whether or not a product is in condition to be used or consumed, this product being intended to be preserved under temperature conditions and for a period of time which limit its degradation.

BACKGROUND

A method for systematically and automatically checking a product, whose preservation in a distribution network depends on the temperature, in particular a product subject to a cold chain, was described in the international patent application published under number WO 03/025529.

In the method described in this previous application, a marker is provided which changes the condition when the temperature of the product exceeds a certain temperature threshold, or when the preservation conditions deviate from a certain reference level, these conditions being either the exceeding of a certain temperature threshold for a period of time longer than a certain period of time or the exceeding of a certain preservation period of time.

In other words, the method described in this previous document provides for indications that depend on an exceeding of certain time or temperature thresholds or limits.

Heat-sensitive products, and in particular food products, are products which continuously depend on the link between time and temperature. The existence of a preservation temperature is only a recommendation making it possible to guarantee a period of time for using the product.

This is the case particularly for fresh food products.

In fact, standards, particularly those relating to food products, require a consume-by or use-by date, which depends on the temperature and preservation time conditions. For example, for a product that should be preserved at 0° C. to +4° C., the consume-by date determined by the authorities incorporates the exposure of the product, for a longer or shorter period of time, to a higher temperature (+8° C.) corresponding to a reasonable break in the cold chain (AFNOR standard NF V 01-003).

The present invention starts from the observation that the use-by dates are generally not optimal because they are determined based on presupposed preservation conditions. For example, for a perishable product that should be preserved at 0° C. to +4° C., its period of use may be extended compared to what the standard indicates if the product is not exposed to temperatures higher than +4° C., insofar as the said standard provides for an exposure to a temperature of +8° C. for a break in the cold chain. This means that some products are not consumed even though they might be, which constitutes a significant drawback both in practical and in economic terms.

SUMMARY OF THE INVENTION

Thus, in the method according to the present invention, an indicator, having characteristics depending on the time and temperature which are similar to the corresponding characteristics of the product, is combined with the perishable product. This indicator is such that it provides information about the possibility of use or consumption of a perishable product depending on the preservation conditions of the product;

so that the indicator provides information enabling the product to be used or consumed for a longer period of time if the product has been preserved under conditions better than the standard conditions, and so that the indicator provides information enabling the product to be used or consumed for a shorter period of time if the product has been preserved under conditions worse than the standard conditions.

Thus, with this method, the use-by or consume-by date varies as a function of the real temperature and preservation period conditions of the product; the consume-by date or the optimal use-by date recorded by the manufacturer at the time of packaging the perishable product becomes dynamic and thus depends on the real conditions of the product. For example, for a food product, the preservation period of time shall be reduced if the temperature conditions degrade and, by contrast, the use-by date shall be increased if the temperature conditions are better, as FIG. 15 also illustrates.

Under these conditions, the use-by date may be considerably prolonged compared to that provided by the regulations. By way of example, a fresh product having a certain consume-by date, perhaps frozen by the consumer, once it has been frozen, the product can be preserved for several weeks, even several months, and may therefore be consumed well beyond the use-by date indicated on the perishable product, as illustrated in FIG. 16. The method, as described, takes into account the real degradation of the product before freezing, no longer continues during the freezing phase and indicates after thawing that the product can be consumed, until the indication of a change in the condition, information about which the consumer does not now have.

Let us suppose that a consumer buys a perishable product whose consume-by date is 7 days after the packaging date under normal preservation conditions. Let us suppose that he decides to freeze the product 2 days before the expiration of the consume-by date. Since freezing at −18° C. stops the microbiological degradation of the product, the consumer may decide one month later to thaw his product and to consume it in the next few days. The consumer thus does not have any information enabling him to know until when he can consume the perishable product. As described, the method makes it possible to respond to this problem because it takes into account the real degradation of the product before, during and after the freezing. Thus, the consumer will have an indicator, which, in the absence of change in condition, will confirm to him that he can consume the product; and which will signal to him, by a change in condition, that the product should no longer be consumed, if the consumer keeps the product too long in his refrigerator after thawing. This is shown in FIG. 13.

In addition, it is known that refreezing a product which has been thawed is usually strongly advised against, in particular because of the risk of development of the bacteria that were initially present in the product. With the present invention, it is also possible to control this risk because the indicator has characteristics depending on the time and temperature, similar to the corresponding characteristics of the product. Thus, the indicator will follow the same course as the perishable product and it can be refrozen, the change in condition of the indicator thus incorporating all of the periods during which the product is exposed to temperatures leading to its degradation.

However, the present invention is not limited to food products. Other products, such as medications, vaccines, and blood to be transfused, must be preserved within predetermined temperature ranges, and departing from the range (upwards or downwards) may cause the use-by date to advance.

Likewise, if the product is preserved under optimal conditions, the use-by date may be prolonged.

Generally, even though it should be preserved within a certain range of temperatures, if the product has an optimal preservation temperature, then the consume-by or use-by date shall be all the more increased as this optimal temperature draws closer.

It should be noted that compared to the known prior arts, in particular those pertaining to the preservation of food products, the present invention is not limited to the fact the indicator is useful when the preservation temperature of the product exceeds a limit, but it applies under the normal preservation conditions of the product. Therefore, the present invention is more than a simple indicator of exceeding a threshold. Rather, it is a real, dynamic consume-by date, or dynamic use-by date, of a perishable product.

An indicator containing a microbial substance, particularly when the perishable product in question is a food or a biological product, is preferably provided.

In one embodiment, an acid-producing microbial substance indicator is provided, and the activity of this microbial substance is measured by following the course of the pH of the medium, in general, an acidification; so that, as long as the pH has not dropped below a predetermined value, the indicator signals that the product can be consumed; and so that, when the pH drops below a predetermined value, the indicator signals that the product can no longer be consumed.

In this case, to follow the course of the pH in the indicator, casein is added, for example, to the medium containing the microbial substance, which forms a precipitate when the pH drops below the certain value, which changes the appearance of the medium.

Thus, the present invention pertains to a method for determining whether or not a product is in a condition to be used or consumed, this product being intended to be preserved under temperature conditions and for a period of time which limit its degradation, a method in which an indicator is combined with the product, such that it provides a signal indicating that the product can be used or consumed, and then, after the expiration of a preservation period of time, a signal indicating a change in the condition of possible use or consumption of the product, this period of time depending on the preservation conditions of the product, so that the indicator provides information enabling the product to be used or consumed for a longer period of time if the product has been preserved under conditions better than the standard or recommended conditions or for a shorter period of time if the product has been preserved under conditions worse than the standard or recommended conditions.

An indicator containing a microbial substance is preferably provided.

In one embodiment, an indicator containing an acidifying microbial substance is provided, and the signal is produced by means of a developer, indicating the change in condition when the pH of the medium, in which the microbial substance is located, drops below a predetermined value.

In one embodiment, the developer forms a precipitate when the pH drops below the predetermined value.

This developer comprises, for example, casein.

In one embodiment, the developer comprises at least one color indicator.

The color indicator is, for example, selected from among the following group: Alizarine, alizarine sodium sulfonate, alizarine red, benzopurpurine, benzoyl auramine G, benzoylethyl auramine, resorcinol blue, bromochlorophenol blue, bromocresol green, bromophenol blue, carmine acid, 2,4-dinitrophenol, 4-(4-dimethylamino-1-naphthylazo)-3-methoxybenzene sulfonic acid, α-dinitrophenol,β-dinitrophenol, γ-dinitrophenol, disodium 4,4-bis(o-tolytriazeno)-2,2'-stilbene disulfonate, disodium 4,4-bis(p-dimethylaminophenylazo)-2,2'-stilbene disulfonate, 4-(p-ethoxyphenylazo)-m-phenylene-diamine monohydrochloride, ethyl red, ethyl orange, hexamethoxy red, hydroquinol sulfonaphthalein, lacmoid, iodeosin, lasmoid, N,N-dimethyl-p-(m-tolylazo) aniline, 4'-methoxy-2.4-diaminoazobenzene, methyl red, methyl red alphazurin, α-naphthylamine, α-naphthylaminoazobenzene, naphthyl red, oxime blue, 4'-oxy-3'-methyl-2.4-diaminoazobenzene, 4'-oxy-2.4-diaminoazobenzene, 4-phenylazo-1-naphthylamine, parafuchsin-hexa-acetic acid, paranitrophenol, p-ethoxychrysoidine, p-sulfo-o-methoxybenzeneazodimethyl-α-naphthylamine, Congo red, violet red, resazurin, naphthyl red, tetrabromocresol, tetraiodophenol sulfophthalein, aurin acid, dithiozone, chromium blue, bromocresol purple, indigo carmine, cacotheline, calceine, eosin extra, eriochromocyanine, thiazole yellow, eriochromium black T, α-nitro-β-naphthol, orange III, methyl red, rhodamine B, potassium rhodazonate, thymolsulfophthalein, rhodium chloride, trihydroxy-2,6,7-phenyl-9 isoxanthene, thorium oxide, xylene orange tetrasodium salt, anthocyanes, phenolphthalein, benzopurpurine 4B, benzopurpurine B, alpha naphthyl red hydrochloride, litmus, methyl red, mixed indicator, lacmoid.

In one embodiment, for adapting the indicator to the product, at least one of the parameters included in the following group is selected: The nature of the microbial substance, the quantity of this microbial substance, the nature of the nutrients, the quantity of the nutrients, the nature of the elements needed for the production of acid by the microbial substance and the quantity of these elements, the nature of a texturing agent of the medium in which the microbial substance is located and the quantity of this texturing agent, the starting pH of the medium, the parameters affecting the $a_w$ [water activity] of the medium, the nature of the developer used for measuring the drop in the pH and the quantity of this developer, the parameters determining the pH at which this developer changes condition.

The parameters are selected, e.g., so that the signal indicating the change in condition would take place after a predetermined period of time when the product is preserved under the standard or recommended conditions.

The parameters can be selected so that the signal indicating the change in condition would appear when the product can no longer be consumed.

In one embodiment, under the standard or recommended conditions, the parameters of the indicator are selected so that the signal indicating the change in condition would appear after a certain period of time, this period of time being increased by modifying one of these parameters by moving it away from the optimal values for the acidification by the microbial substance.

In one embodiment, the microbial substance is selected from among the family of the lactic acid bacteria, preferably of the genera *Lactobacillus, Enterococcus, Carnobacterium, Leuconostoc* and *Weissella*.

In one embodiment, the microbial substance is selected from among the following species: *Carnobacterium piscicola, Lactobacillus fuchuensis* and *Leuconostoc mesenteroides*.

In one embodiment, the nutrients include a carbon source and a nitrogen source, and, preferably, inorganic salts and/or vitamins and/or trace elements.

The carbon source is selected, for example, from among the sugars of the following group: Glycerol, erythritol, D-arabinose, L-arabinose, ribose, D-xylose, L-xylose, adonitol, β-methylxyloside, galactose, D-glucose, D-fructose, D-mannose, L-sorbose, rhamnose, dulcitol, inositol, mannitol, sorbitol, α-methyl-D-mannoside, α-methyl-D-glucoside, N-acetyl-glucosamine, amygdalin, arbutin, esculin, salicin, cellobiose, maltose, lactose, melibiose, sucrose, trehalose, inulin, melezitose, D-raffinose, starch, glycogen, xylitol, β-gentiobiose, D-turanose, D-lyxose, D-tagatose, D-fucose, L-fucose, D-arabitol, L-arabitol, gluconate, 2-keto-gluconate, 5-keto-gluconate.

The texturing agent is selected, for example, from among those of the following group: agar, agarose, gelatin, xanthan, scleroglucan, guar gum.

In one embodiment, the indicator is inactivated when it is not combined with the product and activated when it is combined with the product.

The inactivation can, for example, be carried out by means of means selected from among the following group: freezing, microencapsulation of the microbial substance and/or nutrients, and dividing into compartments.

In one embodiment, the indicator is activated by a physical action selected from among the following group: pressure variation, temperature variation, variation in wavelength of exposure to radiation.

In one embodiment, the microbial substance can be frozen and thawed.

The present invention also pertains to the application of the method defined above to food type or biological or pharmaceutical products.

The present invention also pertains to the application of the method defined above to food products in which the indicator is parameterized so that the appearance of the signal indicating a change in condition is all the more delayed since the preservation temperature of the product is close to the optimal preservation temperature.

The present invention also pertains to the application of the method defined above to a food product intended to be preserved at temperatures ranging from 0° C. to about +4° C., and in which the indicator comprises a microbial substance having an acidifying activity at temperatures lower than or equal to about +4° C.

The present invention also pertains to a device for determining whether or not a product is in a condition to be used or consumed, this product being intended to be preserved under temperature conditions and for a period of time which limit its degradation, this device comprising at least one indicator intended to be combined with the product, this indicator being such that it provides a signal indicating that the product can be used or consumed, and then, after the expiration of a preservation period of time, a signal indicating a change in the condition of possible use or consumption of the product, this period of time depending on the preservation conditions of the product, so that the indicator provides information enabling the product to be used or consumed for a longer period of time if the product has been preserved under conditions better than the standard or recommended conditions, or for a shorter period of time if the product has been preserved under conditions worse than the standard or recommended conditions.

Preferably, the indicator contains a microbial substance.

In one embodiment, the device comprises an indicator containing an acidifying microbial substance, a developer and means for providing a signal indicating the change in condition when the pH of the medium, in which the microbial substance is located, drops below a predetermined value.

The developer is, for example, such that it forms a precipitate when the pH drops below the predetermined value.

In one embodiment, the developer comprises casein.

In one embodiment, the developer comprises at least one color indicator.

In one embodiment, the color indicator is included in the following group: Alizarine, alizarine sodium sulfonate, alizarine red, benzopurpurine, benzoyl auramine G, benzoylethyl auramine, resorcinol blue, bromochlorophenol blue, bromocresol green, bromophenol blue, carmine acid, 2,4-dinitrophenol, 4-(4-dimethylamino-1-naphthylazo)-3-methoxybenzene sulfonic acid, α-dinitrophenol, β-dinitrophenol, γ-dinitrophenol, disodium 4,4-bis(o-tolytriazeno)-2,2'-stilbene disulfonate, disodium 4,4-bis(p-dimethylaminophenylazo)-2,2'-stilbene disulfonate, 4-(p-ethoxyphenylazo)-m-phenylene-diamine monohydrochloride, ethyl red, ethyl orange, hexamethoxy red, hydroquinol sulfonaphthalein, lacmoid, iodeosin, lasmoid, N,N-dimethyl-p-(m-tolylazo) aniline, 4'-methoxy-2.4-diaminoazobenzene, methyl red, methyl red alphazurin, α-naphthylamine, α-naphthylaminoazobenzene, naphthyl red, oxime blue, 4'-oxy-3'-methyl-2.4-diaminoazobenzene, 4'-oxy-2.4-diaminoazobenzene, 4-phenylazo-1-naphthylamine, parafuchsin-hexa-acetic acid, paranitrophenol, p-ethoxychrysoidine, p-sulfo-o-methoxybenzeneazodimethyl-α-naphthylamine, Congo red, violet red, resazurin, naphthyl red, tetrabromocresol, tetraiodophenol sulfophthalein, aurin acid, dithiozone, chromium blue, bromocresol purple, indigo carmine, cacotheline, calceine, eosin extra, eriochromocyanine, thiazole yellow, eriochromium black T, α-nitro-β-naphthol, orange III, methyl red, rhodamine B, potassium rhodazonate, thymolsulfophthalein, rhodium chloride, trihydroxy-2,6,7-phenyl-9 isoxanthene, thorium oxide, xylene orange tetrasodium salt, anthocyanes, phenolphthalein, benzopurpurine 4B, benzopurpurine B, alpha naphthyl red hydrochloride, litmus, methyl red, mixed indicator, lacmoid.

In one embodiment, at least one of the parameters of the indicator is such that the indicator is adapted to the product, the parameters being included in the following group: The nature of the microbial substance, the quantity of this microbial substance, the nature of the nutrients, the quantity of the nutrients, the nature of the elements needed for the production of acid by the microbial substance and the quantity of these elements, the nature of a texturing agent of the medium in which the microbial substance is located and the quantity of this texturing agent, the starting pH of the medium, the parameters affecting the $a_w$ [water activity] of the medium, the nature of the developer used for measuring the drop in the pH and the quantity of this developer, the parameters determining the pH at which this developer changes condition.

In one embodiment, the indicator is such that the parameters are such that the signal indicating the change in condition would appear after a predetermined period of time when the product is preserved under the standard or recommended conditions.

In one embodiment, the device comprises an indicator in which the parameters are such that the signal indicating the change in condition appears when the product can no longer be consumed or used.

In one embodiment, the microbial substance is selected from among the family of the lactic acid bacteria, preferably of the genera *Lactobacillus, Enterococcus, Carnobacterium, Leuconostoc* and *Weissella*.

In one embodiment, the microbial substance is included in the group of following species: *Carnobacterium piscicola, Lactobacillus fuchuensis* and *Leuconostoc mesenteroides*.

In one embodiment, the nutrients include a carbon source and a nitrogen source, and, preferably, inorganic salts and/or vitamins and/or trace elements.

The carbon source is selected, for example, from among the sugars of the following group: Glycerol, erythritol, D-arabinose, L-arabinose, ribose, D-xylose, L-xylose, adonitol, β-methylxyloside, galactose, D-glucose, D-fructose, D-mannose, L-sorbose, rhamnose, dulcitol, inositol, mannitol, sorbitol, α-methyl-D-mannoside, α-methyl-D-glucoside, N-acetyl-glucosamine, amygdalin, arbutin, esculin, salicin, cellobiose, maltose, lactose, melibiose, sucrose, trehalose, inulin, melezitose, D-raffinose, starch, glycogen, xylitol, β-gentiobiose, D-turanose, D-lyxose, D-tagatose, D-fucose, L-fucose, D-arabitol, L-arabitol, gluconate, 2-keto-gluconate, 5-keto-gluconate.

In one embodiment, a texturing agent is included among those of the following group: agar, agarose, gelatin, xanthan, scleroglucan, guar gum.

In one embodiment, the indicator is inactivated when it is not combined with the product and activated when it is combined with the product.

In one embodiment, the inactivation can be carried out by means of means included in the following group: freezing, microencapsulation of the microbial substance and/or nutrients, and dividing into compartments.

In one embodiment, the indicator is activated by a physical action selected from among the following group: pressure variation, temperature variation, variation in wavelength of exposure to radiation.

In one embodiment, the microbial substance can be frozen and thawed.

In one embodiment, the indicator is in the form of a label, and preferably a self-adhesive label.

In one embodiment, the indicator comprises at least one face, one zone of which makes it possible to observe the signal produced by the developer.

In one embodiment, the label comprises a plurality of internal compartments, for example, capsules, making it possible to separate one or more constituents of the component from others for a certain period of time, the walls of the said compartments being able to be broken by any suitable means, for example, by pressing on the label.

BRIEF DESCRIPTION OF THE DRAWINGS

Other features and advantages of the present invention will become evident from reading the description of different embodiments, the description being provided with reference to the attached drawings, in which.

DETAILED DESCRIPTION OF THE INVENTION

Figure 1:
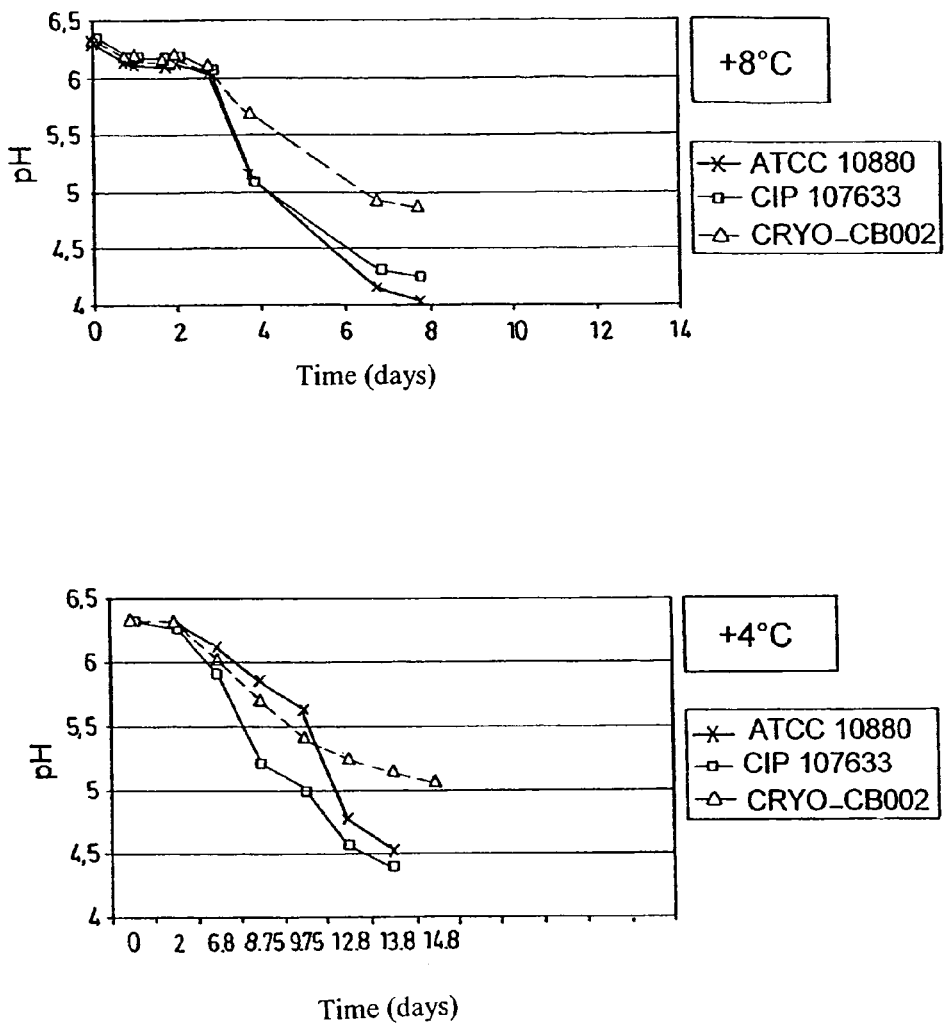
FIG. 1 shows the acidification of the medium by different strains at low temperatures as a function of the time.

The determination of the consume-by date or optimal use-by date of a perishable product is recalled here (AFNOR standard NF V-01-003). For a perishable product, the shelf life is determined as a function of the average preservation temperatures.

The AFNOR standard NF V-01-003, validated in February 2004, pertaining to the hygiene and the safety of food products provides the guidelines for setting up an aging test protocol for the validation of the microbiological shelf life of perishable, refrigerated foods. It describes a method of evaluation of the consume-by date or the optimal use-by date of a microbiologically perishable product.

The standard specifies that the consume-by date or the optimal use-by date of a perishable product must be determined by taking into account the degree of control of the cold chain at the various intervening parties (manufacturer, transporter, distributor and consumer). This use-by date is therefore determined as a function of the average conditions, generally observed along the cold chain during the preservation of a product.

This standard defines three illustrative cases for determining this use-by date as a function of the estimated level of control of the cold chain.

If the cold chain is completely under control, the use-by date is determined for a product that is preserved for its entire shelf life at the optimal temperature (+4° C., for example, for the majority of food products).

If the cold chain is partially under control, the use-by date is determined for a product that is preserved two thirds of the duration of its shelf life at the optimal temperature (for example, +4° C.) and one third of the duration at the reasonable temperature of a break in the cold chain (in general, +8° C.).

If the cold chain is insufficiently under control, the use-by date is determined for a product that is preserved one third of the duration of its shelf life at the optimal temperature and two thirds of the duration at the reasonable temperature of a break in the cold chain.

Thus, the consume-by date or optimal use-by date of a product is a value fixed a priori as a function of statistical data and presupposed preservation conditions, this date being fixed and not depending on the real preservation conditions of the perishable product. The problem is that this use-by date is a static value which cannot account for the real shelf life of the product because its mode of determination presupposes the level of control of the cold chain exerted on a product by the various intervening parties (manufacturer, transporter, distributor and consumer). Therefore, this use-by date only constitutes a theoretical and statistical indication of the sanitary condition of the perishable product after a given period.

The method makes it possible to provide a solution to this problem and to reduce the health risks by dynamically giving the consume-by date or the optimal use-by date for each product individually depending on the preservation conditions to which the product will have actually been subject.

The indicator may be parameterized to develop identically for the product under the same preservation conditions. Thus, the consume-by date or the optimal use-by date of the product is given by the indicator and depends on the real preservation conditions of the perishable product.

In a first application the indicator can be parameterized to change condition on the consume-by date or use-by date of a perishable product as is determined according to AFNOR standard NF V-01-003. If the preservation conditions of the product are worse than the average conditions provided by this standard, the indicator signals that the product can no longer be consumed before the initially provided date; if the preservation conditions of the product are better (optimal preservation temperature without any break in the cold chain or freezing of the product) than the average conditions provided, the indicator signals that the product can always be consumed beyond the date initially provided.

In a second application, by relying on a study of the specific microbiological degradation of each product, the indicator can be parameterized to develop identically to the product depending on its preservation conditions (time and temperature) and thus completely replacing the consume-by date or the optimal use-by date of the product as is determined according to the current standards and as the consumer knows it today. This is made possible by a parameterization of the indicator based on the rate of real microbiological degradation of the product.

There are many products that are perishable and susceptible to degradation or to alteration, microbiological or not, depending on their period of time and their preservation temperature. These are preferably fresh or quick-frozen food products, for example, those sold in a store or distributed by catering companies (delivered hot or cold), medications (vaccines, eye lotions), medically active substances (blood), heat-sensitive chemical products (diagnostic reagents or analytical reagents, photographic developers), cosmetic products, cut flowers or sensitive consumable products (wines, mineral waters, cigars). Each of these products has its own sensitivity and its own degradation kinetics depending on the preservation temperature and duration and therefore its own consume-by date or optimal use-by date under the recommended preservation conditions. A few examples are given in Table 1 below:

TABLE 1

| PRODUCT | PRESERVATION | |
|---|---|---|
| | Temperature | Duration |
| Cut of poultry | 0° C. to +4° C. | 7 days |
| Potted meat | 0° C. to +4° C. | 29 days |
| Pieces of larding bacon | 0° C. to +4° C. | 50 days |
| Ready-cooked dishes cold delivery | 0° C. to +3° C. | 1 to 6 days |
| Ready-cooked dishes hot delivery | >+63° C. | A few hours |
| Blood | +2° C. to +8° C. | 42 days |
| Vaccines | +2° C. to +8° C. | 2 to 6 months |
| Mineral water | +18° C. to +20° C. | 15 days after opening |
| Chocolate | +8° C. to +18° C. | 12 months |
| Antithrombotic agents | +15° C. to +25° C. | 24 months |

The indicator according to the present invention can be parameterized in order to cover the different consume-by date or optimal use-by date corresponding to the perishable products, so that its change in condition takes place on the date provided if the product is preserved under conditions that have been selected to fix this use-by date.

Figure 14A:
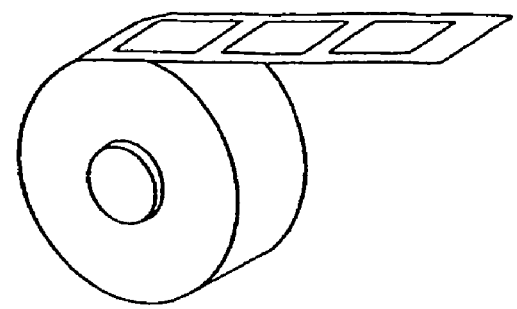
FIG. 14 shows a roll of indicators according to the present invention and means for combining the indicators with the products.
Figure 14B:
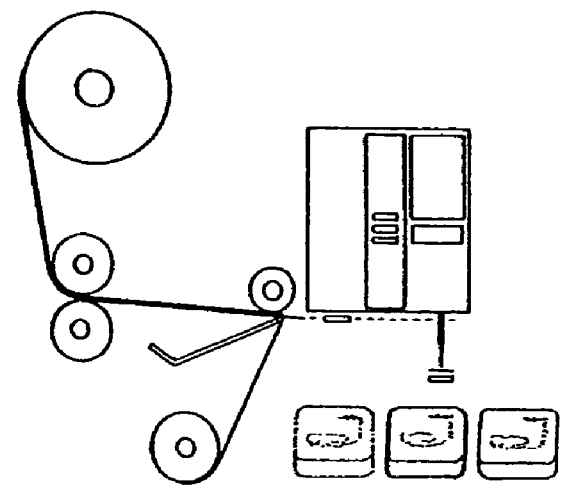
Figure 14C:
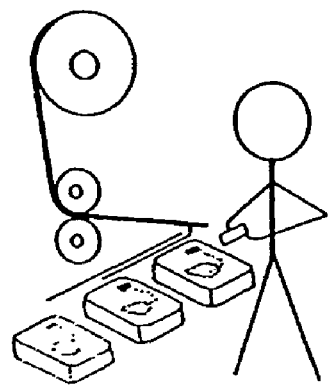
Figure 15:
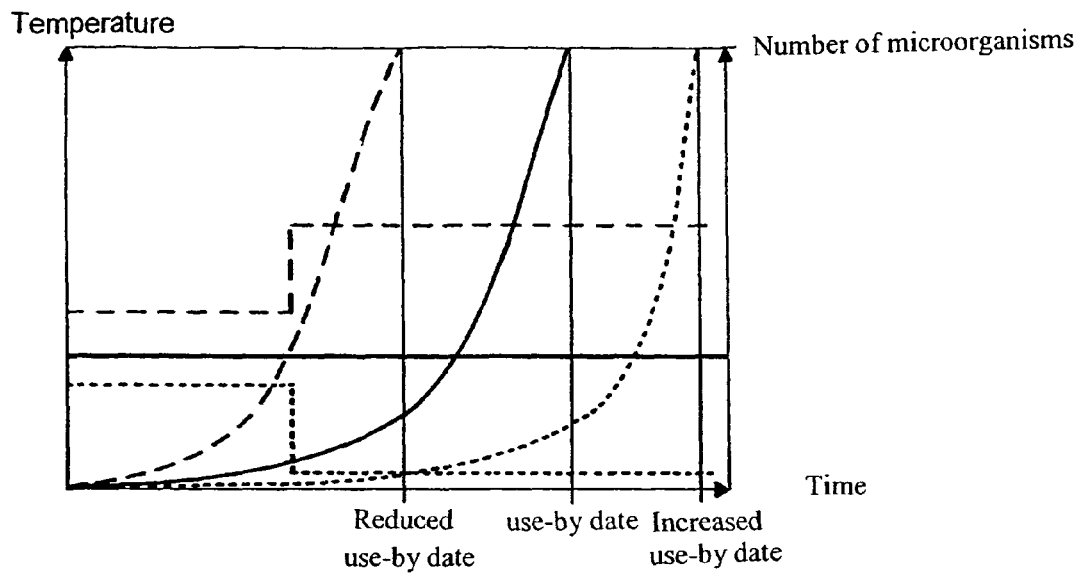
FIGS. 15 and 16 are graphs illustrating use examples of the method according to the present invention.
Figure 16:
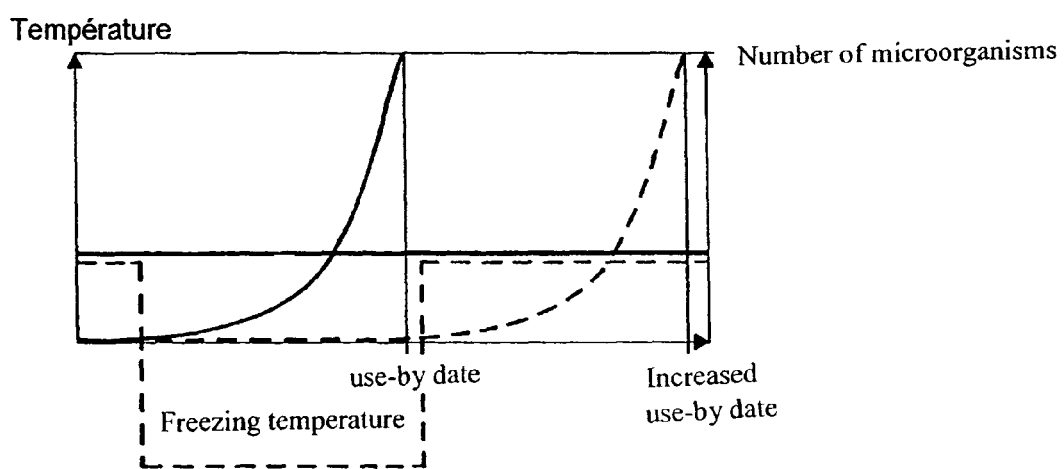

The Indicator:

The indicator is in the form of a transparent label having a reduced thickness and a surface adapted to the use and to the product on which it will be affixed. According to one embodiment, the label is self-adhesive and its surface is the size of a bar code in order to be applied on the same surface as described in the previous patent application WO 03/025529. The thickness of the label is preferably as sufficiently reduced as possible in order to be discreet and to become integrated into the product (or into the packaging) on which it is affixed and in order not to obstruct the reading of the information that it covers. In one embodiment, the self-adhesive labels are delivered in rolls, as shown in FIG. 14a, which can be used on an automatic or manual packaging assembly line and are applied by hand as shown in FIG. 14c or by means of an industrial labeling machine, as shown in FIG. 14-b. According to this embodiment, the manufacture and use of the indicator are carried out at high speed and at reasonable costs in order to meet the needs and constraints of the industry and mass production.

Figure 12:
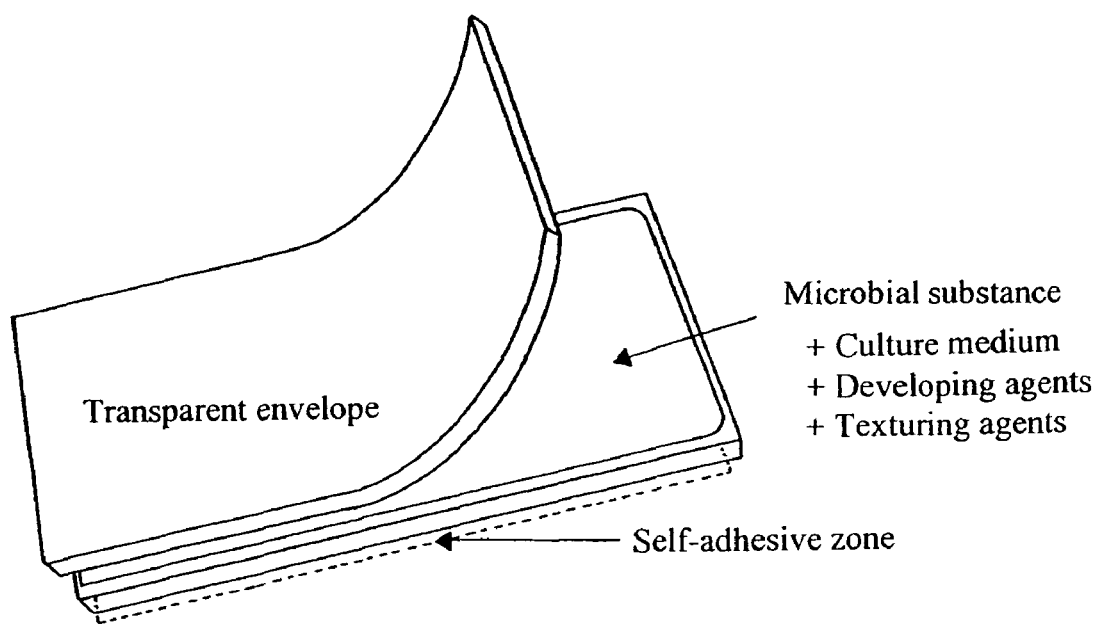
FIG. 12 shows a label according to the present invention.
Figure 13:
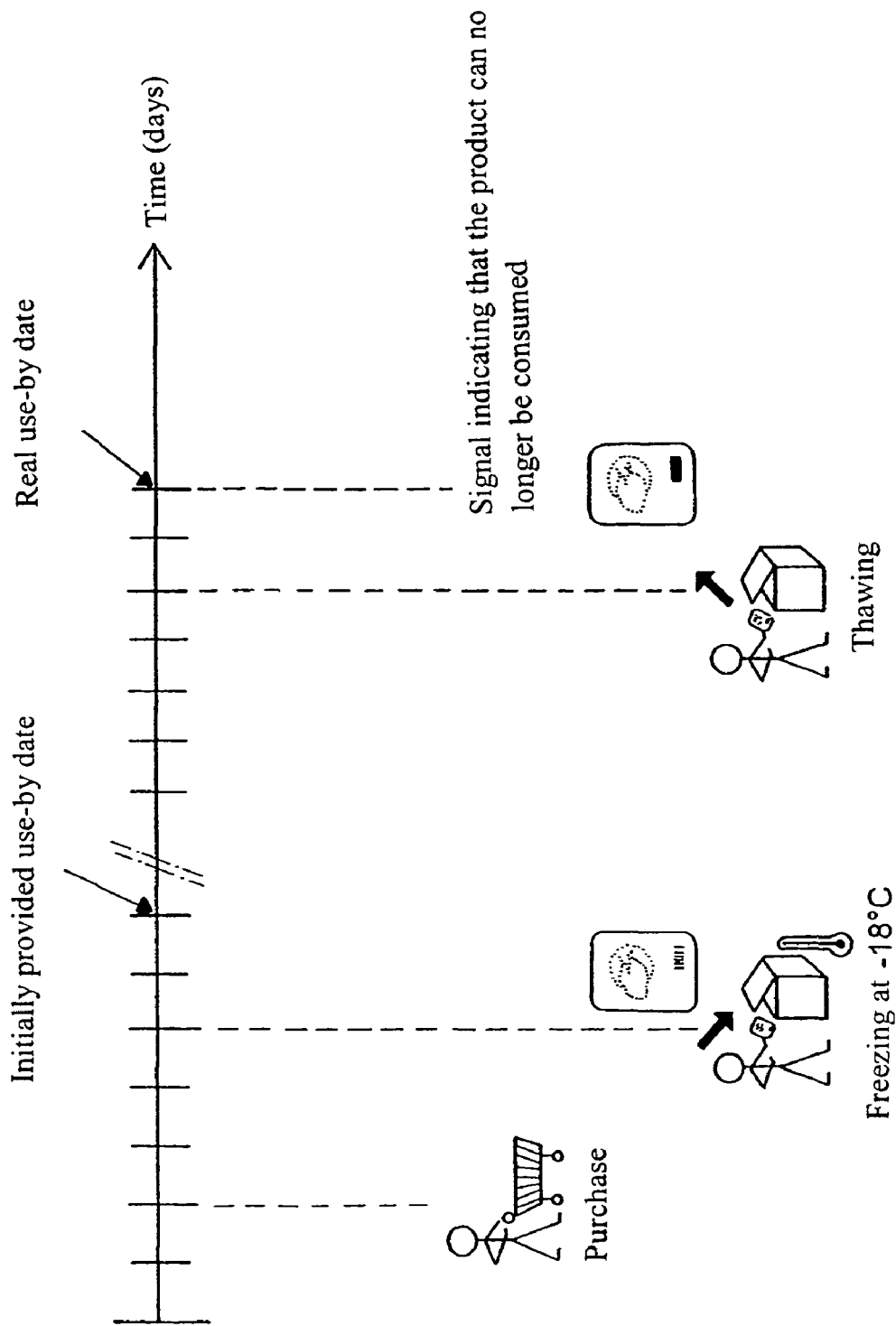
FIG. 13 shows one advantage of the present invention.

Therefore, the indicator comprises a transparent envelope, which is optionally self-adhesive, containing an acidifying microbial substance, a culture medium, the elements for developing the acidification, and one or more texturing agents, as indicated in FIG. 12.

The transparent envelope of the indicator is, for example, made of at least one of the following materials: Polyethyleneterephthalate (PET), polyethylene (PE) and polypropylene (PP).

Microbial Substance:

The microbial substances used in the indicator can be various kinds. Preferably, a microbial substance is used, which varies the pH of the medium in which it is located, and, preferably, this microbial substance is a microorganism which produces acid during its growth or its development or via its metabolic activity. The acidifying microbial substance is preferably nonpathogenic and nontoxic. It is, for example, used in the composition of food products (positive or technical microbial substance).

Moreover, the microbial substance exhibits an acidifying activity at temperatures which are compatible with the preservation temperatures and periods of the products. Its acidification kinetics is also compatible with these preservation temperatures and periods and is in keeping with the degradation kinetics of the perishable products.

Many acidifying microorganisms, for example, bacteria, and in particular lactic acid bacteria can be used for the indicator according to the present invention. The latter family of bacteria is used for the transformation and preservation of many food products: The majority of the lactic acid bacteria do not, therefore, exhibit any risk to consumption. The great majority of these bacteria are food grade. They are so-called positive flora, whose harmlessness is usually ensured. Thus, it is possible to combine them, without risk, with consumable products.

The lactic acid bacteria produce acid (essentially lactic acid) during their growth and during their metabolic activity. Therefore, these bacteria acidify the medium in which they are developing. These acidifying properties are known and used in very many agricultural and food applications.

The lactic acid bacteria develop naturally in many perishable food products at temperatures and at growth rates that are close to degradation flora and pathogenic flora. Therefore, the use of lactic acid bacteria makes it possible to reflect the contamination and microbiological degradation kinetics of the products on which the indicator is affixed.

In the family of the lactic acid bacteria, the strains are selected whose behavior, depending on the temperatures and growth rates, corresponds best to the development kinetics of the microorganisms degrading the perishable products. It is important that the rates and the temperatures at which the microorganisms develop, or have an acidifying metabolic activity, are compatible with the preservation temperatures of the perishable product and compatible with the degradation or alteration kinetics of these products.

Perishable products are generally preserved in a cold state (between 0° C. and +4° C.), but they are capable of being exposed to higher temperatures during a break in the cold chain. Strains of psychrotrophic lactic acid bacteria, while remaining relatively mesophilic, are selected for the indicator. They are strains which are capable of living, developing or having an acidifying metabolic activity at temperatures generally ranging from 0° C. to +45° C. According to a preferred embodiment, the growth or acidifying metabolic activity must be of increasing intensity from 0° C. to +37° C. so that the rate of growth of these strains (or intensity of their acidifying metabolic activity) is compatible with the degradation kinetics of the perishable product.

By definition, mesophilic bacteria are bacteria which can live at temperatures ranging from +20° C. to +45° C. and whose development is optimal at +37° C. Psychrotrophic bacteria are bacteria whose development is optimal at temperatures ranging from +20° C. to +30° C., but which can live and develop at 0° C. Psychrophilic bacteria are bacteria which can live at temperatures ranging from −5° C. to +30° C. and whose development is optimal at +15° C. Cryophilic bacteria are bacteria which develop in cold media.

The growth characteristics of 131 strains of lactic acid bacteria, for example, among the genera *Lactobacillus, Enterococcus, Carnobacterium, Leuconostoc* and *Weissella* were studied within the framework of the present invention. Strains capable of growing at low temperatures (from 0° C. and at least +4° C. and +8° C.) were retained. Then, the cardinal values (depending on the temperature, on the pH and on the $a_w$) of the strains were measured, yielding the best results.

Figure 2:
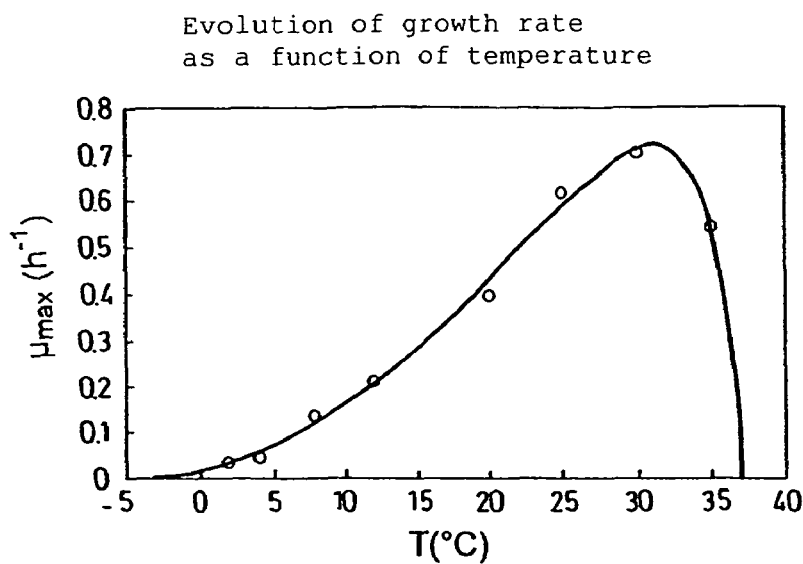
FIG. 2 shows the growth of the strain CRYO-CB002 at different temperatures.

Among these strains, some of them are particularly effective for the indicator: In particular, two strains of the species *Carnobacterium piscicola*, the strain CRYO-CB001 and the strain CRYO-CB002 isolated by the inventors and registered under numbers CNCM I-3297 and CNCM I-3298, respectively, in the National Microorganism Culture Collection of the Pasteur Institute; a strain of *Lactobacillus fuchuensis* coming from the Collection of the Pasteur Institute (registration number CIP 107633); a strain of *Leuconostoc mesenteroides* coming from the ATCC collection (registration number ATCC 10880); these strains can be used because of their acidifying metabolic activities at low temperature. FIG. 1 shows the acidification of the medium at +4° C. and +8° C. for the indicator parameterized as follows: Glucose 20 g/L—tryptone 10 g/L—yeast extract 5 g/L—Tween 80 1.08 g/L—anhydrous dipotassium phosphate 2.6 g/L—anhydrous magnesium sulfate 0.222 g/L—anhydrous manganese sulfate 0.055 g/L—pH 6.2—starter $10^4$ CFU/mL. For example, the strain CRYO-CB002 is capable of growing at temperatures ranging from −4° C. to +37° C., as shown in FIG. 2, while being resistant at temperatures lower than −80° C. and higher than +47° C. in the indicator. This makes it possible to cover the majority of the temperatures that can be found during the preservation of a perishable product and especially a fresh food product.

For other embodiments, strains of bacteria having different growth or acidifying metabolic activity kinetics depending on the temperature shall be selected and used. For example, strictly mesophilic bacteria (being capable of developing at temperatures ranging from +20° C. to +45° C.) having a very slow acidifying metabolic activity at lower temperatures are selected for a product that should be preserved at temperatures ranging from +18° C. to +20° C.

Likewise, mesophilic bacteria (for developing exposure to temperatures higher than +25° C.) are selected for a product that should be preserved at temperatures ranging from +15° C. to +25° C., and they are combined with cryophilic bacteria, developing more quickly at low temperatures (for developing exposure to temperatures lower than +15° C.); the indicator, thus obtained, develops faster at temperatures higher than +25° C. and lower than +15° C.

The kinetics of the acidification of the medium contained in the indicator, by the microbial substance, depends on the metabolism of this substance but it depends on the quantity of microbial substance introduced into the indicator as well. Generally, the greater the quantity of the microbial substance introduced into the indicator is, the faster the acidification of the medium that contains it will be (for a given temperature). Conversely, the smaller the quantity of microbial substance introduced into the indicator, the slower the acidification of the medium will be. This is true for a given formulation of the medium.

Therefore, this means that the course of the indicator depends on the type but also on the quantity of microbial substance that it contains. Thus, depending on the embodiments, more or less microbial substance can be introduced into the indicator so as to obtain an acidification of the medium and therefore a faster or slower signal of a change in condition.

Growth Medium

The indicator contains an acidifying microbial substance. This microbial substance must therefore be located in a medium enabling its development, its growth or its acidifying metabolism.

For example, when lactic acid bacteria are used, the indicator must contain a culture medium that enables the bacteria to survive and grow but also enabling the production of acid by the metabolism of these bacteria.

Generally, for a good development of bacteria, the culture medium must contain a carbon source (in general, a sugar), a nitrogen source (in general of protein origin), inorganic salts, various vitamins, trace elements or essential fatty acids.

For their growth, the strains of lactic acid bacteria can be cultivated on a medium containing different carbon sources. For example, the following sugars can be used for the growth of the strains CRYO-CB001 and CRYO-CB002: Glycerol, ribose, galactose, D-glucose, D-fructose, D-mannose, mannitol, □-methyl-D-glucoside, N-acetyl-glucosamine, amygdaline, arbutin, esculin, salicin, cellobiose, maltose, lactose, sucrose, trehalose and □-gentiobiose.

The sugar contained in the medium, for example, glucose, is also used for the production of lactic acid by the bacteria. It is therefore also necessary for the acidifying activity of the bacterium. This means that the indicator must contain a sugar that can be used by the bacterium for its acidifying metabolism, for example, glucose or fructose.

Figure 3:
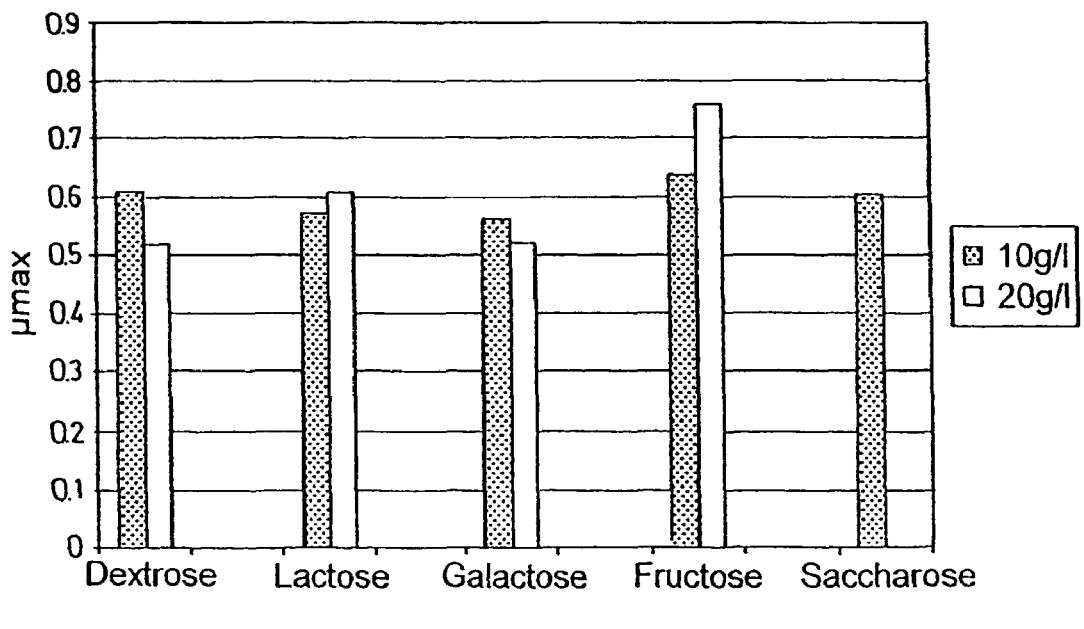
FIG. 3 shows the rate of growth of the strain CRYO-CB002 with 10 or 20 g/L of glucose, lactose, galactose, fructose or sucrose.

The nature of the sugars that can be used by the bacterium, for example, glucose, fructose, lactose, galactose or sucrose, change the rate of growth of the bacteria, for example, of the strain CRYO-CB002, as shown in FIG. 3, and the kinetics of acidification of the medium.

In a preferred embodiment, glucose is used for the growth and the acidifying activity with the strains CRYO-CB002 and CRYO-CB001.

A nitrogen source is also necessary for the growth of the lactic acid bacteria. Different sources, for example, tryptone, peptone or any compound of protein origin can be used. The type and the quantity of the nitrogen source contained in the medium affect the development of the bacteria.

Tryptone and peptone can be used in the indicator at concentrations of 1% or 2% by weight (w/w), alone or combined.

According to a preferred embodiment with the strain CRYO-CB002, a medium containing 1% peptone has been validated, and according to another preferred embodiment with the same strain, a medium containing 1% tryptone has been validated.

As recommended for the MRS (de Man, Rogosa, Sharpe) medium, yeast extract is added to the medium; likewise, salts (for example, NaCl, $K_2HPO_4$ and $MgSO_4$) necessary for or promoting the growth or metabolism of the lactic acid bacteria can be added.

For example, one medium that is used, as summarized in Table 2 is composed of:

TABLE 2

| | |
|---|---|
| Tryptone | 1% |
| Yeast extract | 0.5% |
| Tween 80 | 0.108% |
| Anhydrous dipotassium phosphate | 0.26% |
| Anhydrous magnesium sulfate | 0.0222% |
| Anhydrous manganese sulfate | 0.0055% |
| Glucose | 2% |

Therefore, the nutrient composition of the medium affects the rate of growth of strains, their acidifying metabolic activity and therefore the parameterization of the indicator.

Finally, the pH of the medium containing the acidifying microbial substance is important. In fact, the pH of the medium must be compatible with the growth and the metabolic activity of the microbial substance, for example, a pH between 9 and 4 for lactic acid bacteria. For example, for the strain CRYO-CB002, the optimum growth pH is 7.1. So that there may be an acidification of the medium by the microbial substance, the starting pH of this medium must be sufficiently high (in general, higher than 6 for lactic acid bacteria), while being compatible with the development and the acidifying metabolism of the microbial substance.

As the acidification kinetics has an effect on the parameterization of the indicator, the starting pH of the medium containing the microbial substance has an effect on this parameterization as well.

Developing of the Acidification:

In the indicator according to the present invention, the degradation of a perishable product is simulated thanks to a microbial substance. The development of the microbial substance and its acidifying metabolism are visualized by the continuation of the acidification of the medium contained in the indicator. The acidification of the medium can be visualized by means of a plurality of developers.

Figure 4:
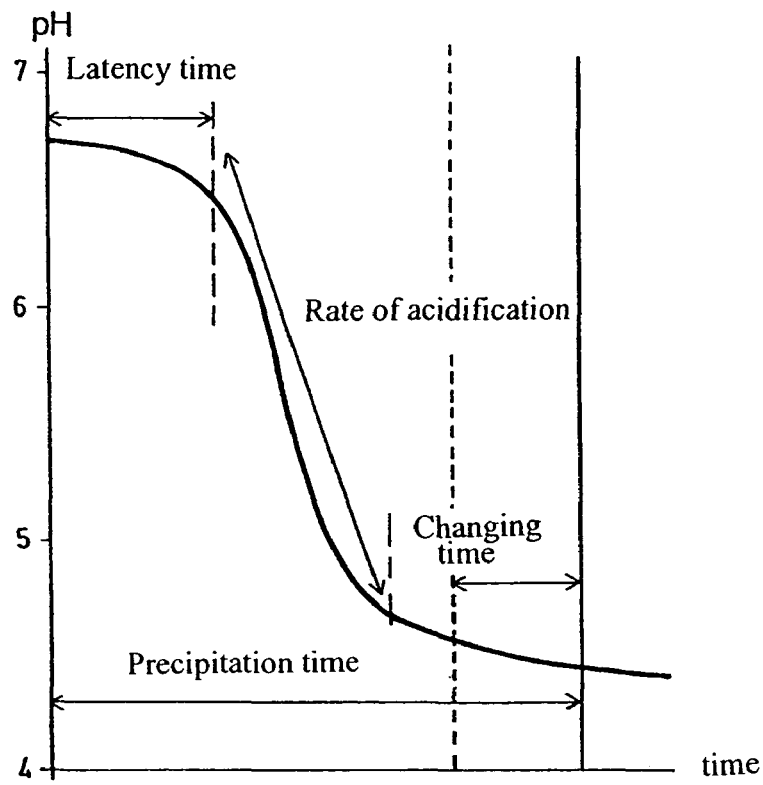
FIG. 4 shows an example of kinetics of acidification of the medium by a lactic bacterium.

The end of the consume-by date or the optimal use-by date of a product is expressed by the indicator when said indicator changes condition. The indicator changes condition when the pH of the medium that contains it drops below a certain value, an example of which is shown in FIG. 4. The dropping of the pH below a certain value is visualized by a change in condition of one or more developers contained in the indicator.

Color indicators are used to visualize the acidification of the medium. The color indicators are weak acids or bases, whose acid and base forms have different colors. Therefore, the color of the indicators changes when the pH of the medium that contains them drops below, or above, the pKi of the indicator.

Thus, the color of the indicator can change at a certain pH if the color indicator that contains it has a pKi equal to the pH in question. One of the benefits of using color indicators is that the signal due to a change in color can be interpreted by the naked eye. Moreover, the change in color takes place clearly and suddenly, which prevents the confusion due to a subjective interpretation.

Many indicators can be used for the method, for example, methyl red, mixed indicator, lacmoid, the anthocyanes, phenolphthalein, 2,4-dinitrophenol, ethyl orange, benzopurpurine 4B, benzopurpurine B, alpha-naphthyl red hydrochloride, litmus, aurin acid, dithiozone, chromium blue, bromocresol purple, indigo carmine, cacotheline, calceine, eosin extra, eriochromocyanine, thiazole yellow, eriochromium black T, α-nitro-β-naphthol, orange III, methyl red, rhodamine B, potassium rhodazonate, thymolsulfophthalein, rhodium chloride, trihydroxy-2,6,7-phenyl-9-isoxanthene, thorium oxide, xylene orange tetrasodium salt.

The following color indicators may also be used in the indicator: Alizarine, alizarine sodium sulfonate, alizarine red, benzopurpurine, benzoyl auramine G, benzoylethyl auramine, resorcinol blue, bromochlorophenol blue, bromocresol green, bromophenol blue, carmine acid, 2,4-dinitrophenol, 4-(4-dimethylamino-1-naphthylazo)-3-methoxybenzene sulfonic acid, α-dinitrophenol, β-dinitrophenol, γ-dinitrophenol, disodium 4,4-bis(o-tolytriazeno)-2,2'-stilbene disulfonate, disodium 4,4-bis(p-dimethylaminophenylazo)-2,2'-stilbene disutfonate, 4-(p-ethoxyphenylazo)-m-phenylene-diamine monohydrochloride, ethyl red, ethyl orange, hexamethoxy red, hydroquinol sulfonaphthalein, lacmoid, iodeosin, lasmoid, N,N-dimethyl-p-(m-tolylazo) aniline, 4'-methoxy-2.4-diaminoazobenzene, methyl red, methyl red alphazurin, α-naphthylamine, α-naphthylaminoazobenzene, naphthyl red, oxime blue, 4'-oxy-3'-methyl-2.4-diaminoazobenzene, 4'-oxy-2.4-diaminoazobenzene, 4-phenylazo-1-naphthylamine, parafuchsin-hexa-acetic acid, paranitrophenol, p-ethoxychrysoidine, p-sulfo-o-methoxybenzeneazodimethyl-α-naphthylamine, Congo red, violet red, resazurin, naphthyl red, tetrabromocresol, tetraiodophenol sulfophthalein.

According to preferred embodiments, the following indicators are used: The anthocyanes, phenolphthalein, 2,4-dinitrophenol, ethyl orange, benzopurpurine 4B, benzopurpurine B, alpha-naphthyl red hydrochloride, litmus, methyl red, mixed indicator, lacmoid.

According to a particular, preferred embodiment, mixed indicator is used because it has beneficial aesthetic and technical properties. The change in its color takes place at a pH close to the precipitation pH of casein and its colors, green before changing and blue after changing, correspond to a color code that can be used for the general public, in particular in terms of marketing.

However, other color indicators may be used depending on the needs, and in particular the marketing needs, linked with the perishable product and with its packaging.

Another means for visualizing that the consume-by date or optimal use-by date of a perishable product is passed is to make the indicator, which is transparent at the start, opaque.

A method for systematically checking a product whose preservation depends on the cold chain is described in the previous patent application WO 03/025529. The expiration of the product can be systematically detected by the hiding from view a bar code on which the indicator/label is affixed.

In one embodiment, the label hides from view a message on which it is affixed; this message being able to indicate that the product can be consumed or used as long as it is legible.

Casein can be used to make the indicator opaque when there is acidification of the medium.

Casein is one of the principal proteins of milk. More than half of its amino acids carry free ionizable groups. In milk, casein is found in a saline complex in the micellar state. A drop in the pH brings about a precipitation of casein. It precipitates completely to a pH of 4.7 in milk. If the acidification develops progressively in the medium, due to a lactic fermentation, a homogeneous coagulum, such as in yogurt, forms. Thus, the casein soluble in the milk precipitates in the presence of lactic acid and is found in an insoluble form:

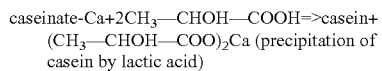

caseinate-Ca+2CH$_3$—CHOH—COOH=>casein+ (CH$_3$—CHOH—COO)$_2$Ca (precipitation of casein by lactic acid)

This reaction is very often used in the food and agriculture industry, during the curdling of milk for the formation of fresh cheese and then salted and aged cheese.

Casein is perfectly suitable for the embodiment of the present invention because it may be in a transparent solution at basic pH, neutral pH (pH 7) or slightly acid pH (higher than its isoelectric point) and because it can form an opaque precipitate at low pH (lower than its isoelectric point). The precipitation point of casein varies depending on the ionic strength of the medium and on the temperature. In the indicator, depending on the saline concentrations selected, casein precipitates at pH values ranging from 5.7 to 5.

In addition, casein is a product that is not very expensive, is food grade and is used in many applications of the food and agriculture industry.

Casein can be extracted from milk by acid precipitation and can then be neutralized by sodium hydroxide (NaOH), potassium hydroxide (KOH) or calcium hydroxide (CaOH). Sodium, potassium or calcium caseinates are then obtained, respectively. Casein can be redissolved by dissolution of these caseinates.

Casein may also be extracted from milk by tangential microfiltration or ultrafiltration. Due to this method, a native casein more or less contaminated by other soluble proteins of the milk, is recovered.

Sodium (Na+), calcium (Ca++), potassium (K+) caseinates or native caseins (which are not precipitated) of different purities can be used for the indicator.

Preferably, sodium caseinate and potassium caseinate concentrations of 5%, 6%, 7%, 8%, 9% and 10% are introduced into the indicator. The native caseins and calcium caseinate have been used at concentrations of 0.5%, 0.75% and 1%. At these concentrations, the different caseins are soluble in a transparent form in the medium. Therefore, they make it possible to read the bar code through the indicator.

The intensity of the precipitate and thus the intensity of the opacification of the indicator depend on the casein concentration. The higher the casein concentration is in the indicator, the greater is the intensity of the opacification. The concentration of the casein in the indicator must be sufficient to permit the opacification of the indicator after precipitation and to prevent the reading of the reading of the bar code or the message placed under the indicator.

Preferably, because of the high intensity of the precipitate obtained, sodium caseinate is used in the indicator. Preferably, this caseinate is used at concentrations ranging from 8% to 10%.

The two types of developers (color indicator and casein) can be used together or separately.

If they are used together, the color indicator can be selected to change color at the same pH as that at which casein precipitates. In this case the signal of one reinforces, or supports, the signal of the other. For example, the color indicator will reinforce the indication or add a signal suitable for the packaging or the tastes of the consumer to the precipitation of the casein.

The two types of developers may also be used together but by selecting a color indicator that changes color at a pH different from the precipitation pH of casein, in order to give two successive messages about the possibility of using or not using a perishable product.

For example, the precipitation of casein may occur first (at pH 5.2) and, by hiding the bar code, may be a signal indicating that the product may no longer be sold (sell-by date) or must be consumed quickly. The changing of the color indicator then occurs (at pH 5 or 4.5) and indicates thus that the product must absolutely no longer be consumed. For this, a color indicator is selected whose changing pH is lower than the precipitation pH of casein, and this difference can be quantified and parameterized.

The reverse may also be embodied, i.e., the use of a color indicator which changes before the casein precipitates, i.e., an indicator which changes color at a higher pH than the precipitation pH of casein.

Figure 11:
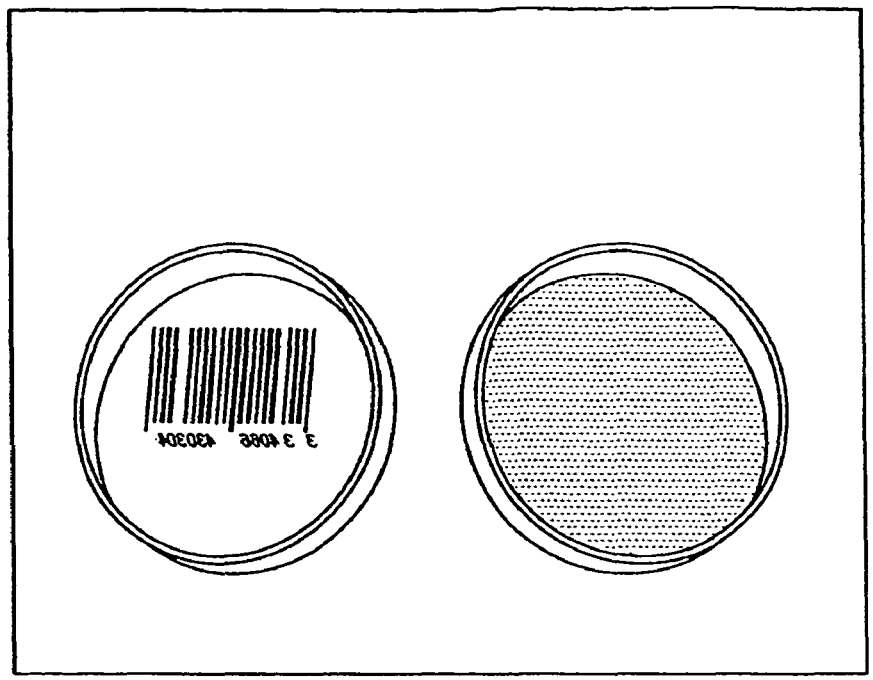
FIG. 11 shows a photo showing the precipitation of casein and the changing of the mixed indicator during the acidification of the medium by lactic acid bacteria.

FIG. 11 shows a photo of an example of precipitation of casein and changing of the mixed indicator following an acidification of the medium according to the present invention (the indicator comprises, in this example, lactic acid bacteria).

Texturing Agents:

The indicator is advantageously in the form of a transparent label of reduced dimensions, the entire container and contents being transparent or translucent. The indicator is relatively supple and homogeneous in order to be adapted to all perishable products and to be applied to all packagings, whose degradation one wants to check.

A texturing agent may be added to the medium in order to give it the desired appearance. The texturing agent selected must permit the development of the microbial substance in the indicator, the acidification of the medium and the developing of this acidification according to the mode selected. Moreover, the texturing agent added must be transparent and, if possible, colorless, dissolved in the medium so as not to interfere with the mode of detection of the acidification, in particular if the method of hiding a bar code is used. Finally, the texturing agent must preferably be of food grade to facilitate a use of the indicator in the food agriculture industry.

According to a preferred embodiment, the texturing agent used is a thickening agent or a gelling agent.

The thickening agents increase the viscosity of a solution. Depending on their concentration and the temperature, they slow down or prevent the flow of the solution that contains them. They are useful in the indicator for keeping the medium in a homogeneous and uniform state.

Gelling agents solidify the solution that contains them, forming a macromolecular network, making possible the formation of a more or less supple and elastic gel depending on the type of the gelling agent, its concentration and the temperature. They are conventionally used in microbiology when a solid substrate is investigated for the growth of bacteria. The gelling of the indicator may be useful for making it possible to keep the medium in a homogeneous and uniform state and prevent flows if the packaging of the indicator is pierced.

The different texturing agents that may be used in the indicator include agar or agarose (at concentrations of 0.5% to 1.6%), different gelatins of different animal origins (porcine, chicken, bovine) and different tissues (skin, bone), xanthan, scleroglucan, guar gum. Table 3 below groups together various texturing agents that may also be used:

TABLE 3

| ORIGIN | TYPE | FUNCTIONALITIES |
|---|---|---|
| Extracts of algae | Alginate | Thickening agent |
| | | Gelling agent |
| | Agarose | Gelling agent |
| Extracts of seeds | Guar | Thickening agent |
| | Carob | Thickening agent |
| Extracts of vegetable subproducts | Pectin | Gelling agent |
| Microorganisms, fermentation | Xanthan | Thickening agent |
| | Gellan | Gelling agent |
| | Scleroglucan | Thickening agent |
| Animal | Gelatin | Gelling agent |

Agarose or agar, gelatin or scleroglucan shall preferably be used.

Generally, the higher the texturing agent concentration is, the more slowly the microbial substance contained in the indicator develops and the slower is the acidification of the medium of the indicator. Thus, the texturing agent concentration has an effect on the parameterization of the indicator.

Figure 5:
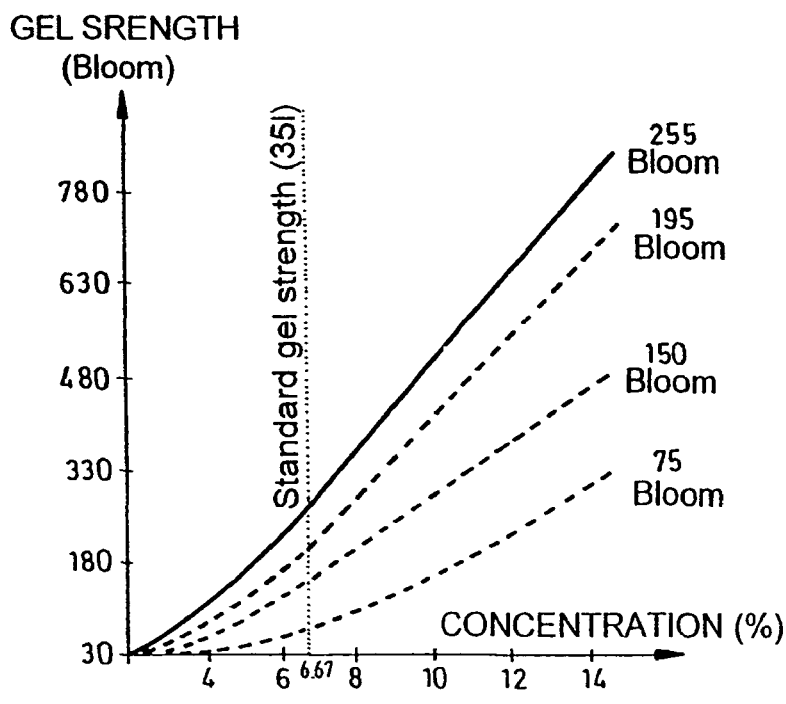
FIG. 5 shows the course of the gel strength as a function of the gelatin concentration and the Bloom strength.

Among the texturing agents that can be used, gelatin has the advantage of being used in the manufacture of many food products and of being food grade. Its cost is relatively not very high, which makes possible a very widespread use. It has various origins (bovine, porcine, chicken, fish). Depending on their origin and their mode of preparation (acid or basic extraction) as well as on the extraction temperature, the gelatins may exhibit different characteristics in terms of gelling power. This characteristic is measured by the Bloom strength. The higher the Bloom strength of a gelatin is, the stronger the gel formed will be at a given concentration. This is illustrated in FIG. 5 (Chene, C., 2000, Gelatin—Theoretical aspects; *Journal de l'ADRIANOR—Agro-Jonction* No. 24). Depending on the type of gelatin selected and on its Bloom strength, the appearance of the indicator may therefore be modified. Thus, a gelatin with a Bloom strength of 310 shall yield a much more solid gel than a gelatin with a Bloom strength of 200 at the same concentration and at the same temperature.

Porcine gelatins 150, 250 and 310, bovine gelatins 150, 250 and 280, chicken gelatin P200 can particularly be used in the indicator at concentrations of 0.125% to 20%.

The stronger the gel formed is, the more slowly the microbial substance develops and thus the slower is the acidification of the medium. Thus, the higher Bloom strength the gelatin possesses, the slower is the acidification of the medium.

Likewise, the more concentrated the gelatin is (regardless of its Bloom strength), the slower is the microbial development and the slower is the acidification of the medium.

Therefore, the Bloom strength of a gelatin and the concentration at which this gelatin is used have an effect on the parameterization of the indicator. Thus, the type and the concentration of the texturing agent used make it possible to vary the appearance of the indicator but also the rate of acidification of the medium. Thus, the texturing agent can be used to parameterize the indicator as a function of the perishable product to be checked.

Activation:

The indicator contains a microbial substance that develops and acidifies the medium more or less quickly depending on the preservation temperature. The indicator is in the form of a label to be fixed to a perishable product. The indicator is parameterized to follow the degradation of the said product with which it is combined. It must be used as the dynamic consume-by date or optimal use-by date. For this, the start of the acidification process must correspond to the start of the consume-by date or the optimal use-by date of the perishable product. For the sake of convenience and for economic reasons, the manufacture of the indicator is uncoupled, in time and in space, from the manufacture and/or the packaging of the perishable product for which it is intended. For this, the microbial development process and the acidification of the medium must be able to be triggered independently of the manufacture.

Two types of methods can be used for uncoupling the manufacture and the activation of the indicator.

Freezing is a method for the reversible inactivation of the microbial development that can be used to stop the growth and metabolism of bacteria contained in the indicator after the manufacture. Once the indicator has been assembled (with the medium containing the microbial substance placed inside the label), the indicator is frozen at negative temperatures (temperatures at which there is no water usually available in the liquid state), e.g., from −18° C. to −80° C. Freezing temperatures lower than −18° C. may be used. Since this temperature corresponds to the freezing standards in force in the food industry and in domestic use, it is therefore used with preference.

Once it has been frozen, the indicator according to the present invention remains stable for several months. No development of bacteria and no acidification of the medium are observed. The indicator may be stored and transported from the manufacturing site to the site of use in this frozen form.

The lactic acid bacteria selected for the indicator according to the present invention support the freezing within the indicator and this freezing does not affect the capacity of the bacteria to develop as soon as they are exposed to temperatures compatible with their growth. Also, the developing system of the indicator is not altered by freezing. Therefore, freezing leaves the indicator intact as regards its active ingredient. It is a completely reversible inactivation method.

The indicator is activated when this indicator is thawed by placing it at a temperature equal to or higher than the temperature at which water can be found in the liquid state, generally at 0° C. This makes microbial development possible again and therefore the acidification of the medium. The process of acidification of the medium and of developing of this acidification then develops identically to the process described above.

The other technique that can be used within the method is a system of conditional activation of the indicator. In this conditional activation system, the manufactured indicator (microbial substance in a medium inside a label) is not directly active. The indicator according to this system must be activated separately from the manufacture by means of a simple physical method. To manufacture an indicator that is conditionally not active and can be activated, the microbial substance must be isolated from the nutrients (and vice versa) to prevent any development of the microbial substance and its acidifying metabolism.

This separation between the microbial substance and the nutrients can be carried out by incorporation of tightly encapsulated bacteria (or else nutrients) within the indicator. This requires the previous manufacture of capsules, or beads, containing the microbial substance (or nutrients). These capsules must be relatively small, impervious and stable in the medium contained within the indicator. Depending on the size of the capsules, one speaks of microencapsulation (mean diameter of the capsules less than 1 mm) or macroencapsulation (mean diameter of the capsules greater than 1 mm). The microbial substance isolated from the rest of the medium by the capsules is then not able to develop or acidify the medium. The indicator is therefore inactive. The indicator thus manufactured remains inactive and stable over time, including at ambient temperature if the capsules are themselves stable at ambient temperature.

To activate the indicator, the microbial substance (or the nutrients) must be released into the medium. For this, the capsules must be broken, if possible, by a simple physical method (pressure, ultraviolet (UV), temperature shock). The microbial substance is then released into the medium and can develop again. Conversely, if the capsules contain the nutrients, once these capsules have been broken, the nutrients are available for the development of the microbial substance and acidification of the medium in the indicator.

The activation of the indicator is very conditional because it occurs when the capsules are broken and when the microbial substance (or the nutrients) is released. Due to this technique, the indicator may be produced on a mass scale, stored and transported at ambient temperature on the site of manufacture or packaging of the perishable product. The indicator can then be activated as required.

There are a plurality of micro- or macroencapsulation techniques that can be used. Complex coacervation, encapsulation by atomization of inverse emulsions or encapsulation by precipitation of sodium alginate are, for example, used. These techniques can be adapted to the specific needs of the present invention: Small size of the capsules, imperviousness and complete stability in aqueous media, breaking via a simple physical method compatible with the industrial and microbiological constraints.

Another way to consider the separation between the microbial substance and the nutrients is to manufacture an indicator consisting of two different compartments. One compartment contains the microbial substance in a medium without nutrients and the other compartment contains the nutrients isolated from the bacteria. The two compartments can be separated by an impervious transparent barrier, this barrier being able to be destroyed or interrupted by a simple physical method. For example, if the barrier is a manufacturing or assembly film that is more fragile than the label containing the indicator, a calibrated force pressure can break the film and put the nutrients and the bacteria in contact with each other.

In the case of a conditional activation system (encapsulation or dividing into compartments) the bacteria must survive and remain stable, including at ambient temperature, in a medium in the absence of nutrients. For example, lyophilized bacteria can be used, or else bacteria in a medium without nutrients and only containing salts.

Parameterization:

The indicator simulates the development of bacteria that are capable of contaminating or of altering the product on which it is affixed.

In one application, the indicator is parameterized as a function of the consume-by date or the optimal use-by date defined by the manufacturer, in general according to the AFNOR standard NF V-01-003: If the product is preserved under the temperature conditions that are those used to define this use-by date, the indicator changes condition on the predefined use-by date; if the product is preserved at optimal temperatures (the least favorable to the degradation of the product and/or to the microbial development) compared to those presupposed by the standard, then the indicator changes condition after the theoretical use-by date; if the product is preserved at temperatures worse than those presupposed by the standard (temperatures promoting the degradation of the product and/or the microbial development), the indicator changes condition before the theoretical use-by date.

In another application, the indicator is parameterized to reflect the degradation, whether or not it is microbiological, of the perishable product. This parameterization follows up, for example, an estimated microbiological study specific to each product or a study of the course of the stability properties of the product. The change in condition takes place when the preservation conditions (time and temperature) of the perishable product lead to a level of alteration and degradation of the said product that is incompatible with its consumption or its use, and independently of the notion of use-by date itself.

The present invention describes an indicator which constitutes a dynamic consume-by date or optimal use-by date of a perishable product.

The rate of growth of the microbial substance and the rate of acidification of the medium by the said microbial substance must be adapted to reflect the degradation of the perishable product as a function of the time and the preservation temperature. This adaptation is carried out by the parameterization of the indicator.

This parameterization may either be:

(i) based on the consume-by date or optimal use-by date of the perishable product determined according to the AFNOR standard NF V-01-003; the indicator then provides a dynamic dimension in relation to this predefined use-by date by signaling that the product can no longer be consumed before this date or, conversely, that the product can be consumed beyond this date, as a function of its real preservation conditions;

(ii) or be based on a real microbiological degradation study of the product and, because the indicator uses bacteria whose behavior reflects the behavior the degradation flora, it may be the exclusive indicator of the level of degradation of the perishable product.

In all the cases, the indicator must be parameterized to develop so as to reflect the level of degradation of the product as a function of its preservation conditions (time and temperature).

The parameterization consists of determining the moment at which the indicator must change condition as a function of the preservation temperature and time, that is, the moment at which the developer or the developers change condition within the indicator.

The parameterization of the developer/pH pair is therefore essential. Thus, we have seen that the selection of the color indicator as a function of its changing pH is decisive.

For a certain developer (for example, mixed indicator and/or sodium caseinate), and under certain ionic strength conditions (saline composition of the medium permitting the development of the microbial substance), the checking of the moment when the pH of the medium drops below a certain threshold is an essential factor of the parameterization. This means that a checking of the kinetics of acidification of the medium by the microbial substance is necessary.

Generally, the faster the kinetics of acidification of the medium is, the more quickly will the indicator change (at a certain temperature). Thus, it is advisable to check the acidification kinetics of the medium in the indicator. To check the acidification kinetics, it is advisable to check mainly the following elements:

(1) the selection of the microbial substance in relation to its capacity to grow at the preservation temperature of the product whose course it will simulate;
(2) the selection of the microbial substance in relation to its capacity to produce acid;
(3) the quantity of microbial substance introduced into the medium;
(4) the quantity of nutrients necessary for the development of the microbial substance;
(5) the quantity of precursor substrate needed for the production of acid by the microbial substance;
(6) all of the parameters may affect the development of the microbial substance;
(7) the starting pH of the medium.

The microbial substance must be selected as a function of its growth kinetics and of its acidifying metabolic activity according to the preservation temperature of the product. For example psychrophilic strains are selected to follow the preservation of products that should be kept between 0° C. and +4° C., such as, for example, the strains CRYO-CB002, CRYO-CB001, CIP 107633, and ATCC 10880.

The more psychrophilic the selected bacterial strain is, the more quickly will the indicator change condition at low temperature (0° C., +4° C. or +8° C.). Likewise, the more slowly the selected strain grows, the slower is its production of acid and the slower will the indicator change condition at a given temperature.

For example, as illustrated in FIG. 1, the strain CIP 107633 acidifies the medium faster at low temperature (+4° C. or +8° C.) than the strain CRYO-CB002. This makes it possible to have an indicator for shorter consume-by or use-by dates in the cold state.

Figure 6A:
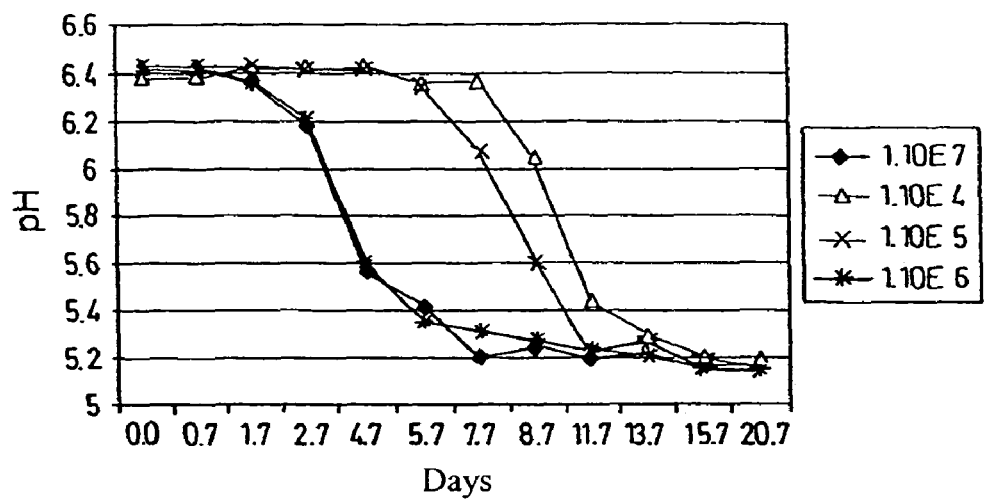
FIG. 6 shows the course of the pH of the medium as a function of different starter quantities of the strain CRYO-CB002 for two cases of preservation conditions.
Figure 6B:
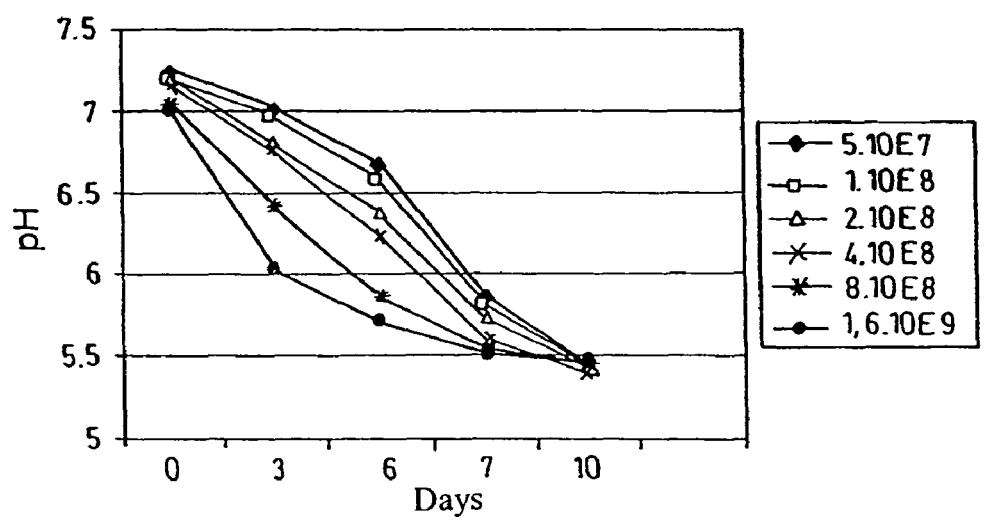

The quantity of microbial substance introduced into the indicator (starter) has an effect on the kinetics of acidification of the medium and therefore on its parameterization. The lower the quantity of microbial substance introduced into the indicator is, the more time is required for the medium to be acidified. Conversely, the greater the quantity of microbial substance introduced into the medium is, the more quickly the medium is acidified (for a given medium formulation). For example, for the strain CRYO-CB002, the acidification is faster at +4° C. for a starter of $1.6 \times 10^9$ CFU per mL than for a starter of $5 \times 10^7$ CFU per mL of medium, as shown in FIG. 6-b (in this example, the indicator comprises 2.5% bovine gelatin with a starting pH of 7.2). With this same strain, under consume-by date conditions of ⅓ at +4° C. and ⅔ at +8° C., the acidification is faster with $1 \times 10^7$ CFU per mL than with $1 \times 10^4$ CFU per mL of medium, as shown in FIG. 6-a (in this example, the indicator comprises 2% chicken gelatin 200 with a starting pH of 6.4).

Thus, for example, for the strain CRYO-CB002 and for a given medium formulation, a starter of $10^5$ CFU per mL makes possible a changing of the color indicator and a precipitation of casein in 11 days at +8° C., while a starter of $10^7$ CFU per mL makes possible a changing and a precipitation in 7 days under the same conditions.

Figure 10:
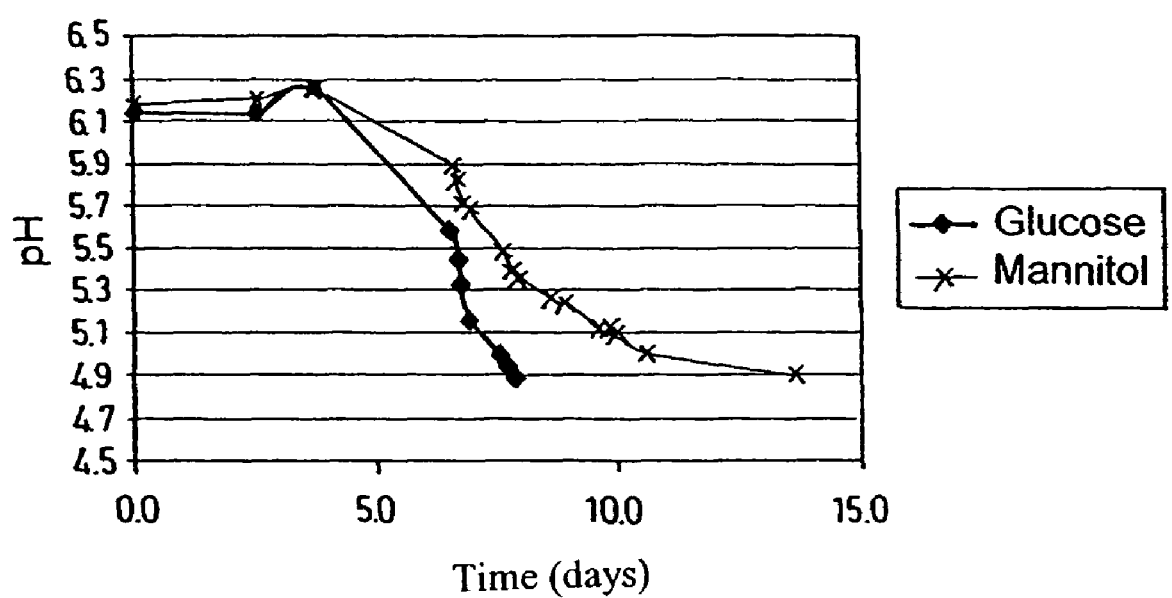
FIG. 10 shows the acidification of the medium by the strain CRYO-CB002 (starter $1\times10^4$ U) in the presence of 2% glucose or 2% mannitol.

The quantity of nutrients makes it possible to check the rate of development of the microbial substance. Thus, the indicator can be parameterized by varying the composition of the medium. For example, the rate of growth of a strain of bacteria (and thus the rate of acidification of the medium) depends on the nutrients present and on their concentration. The more favorable the medium is to the microbial development, the faster will be the acidification of the medium. For example, the use of mannitol leads to an acidification of the medium, by the strain CRYO-CB002, that is slower than in the case of the use of glucose as shown in FIG. 10 (the indicator comprises, in this example, a starter of $1 \times 10^4$ CFU per mL of the strain CRYO-CB002 and 2% glucose or 2% mannitol).

The quantity of substrate needed for the production of acid by the microbial substance makes it possible to check the rate of acidification of the medium. In fact, if the precursor substrate of the manufactured acid (for example, a fermentable sugar and, for example, glucose for a strain of a lactic bacterium) is a limiting condition, more time will be required for the microbial substance to produce enough acid to make the pH drop below a certain threshold.

Figure 7:
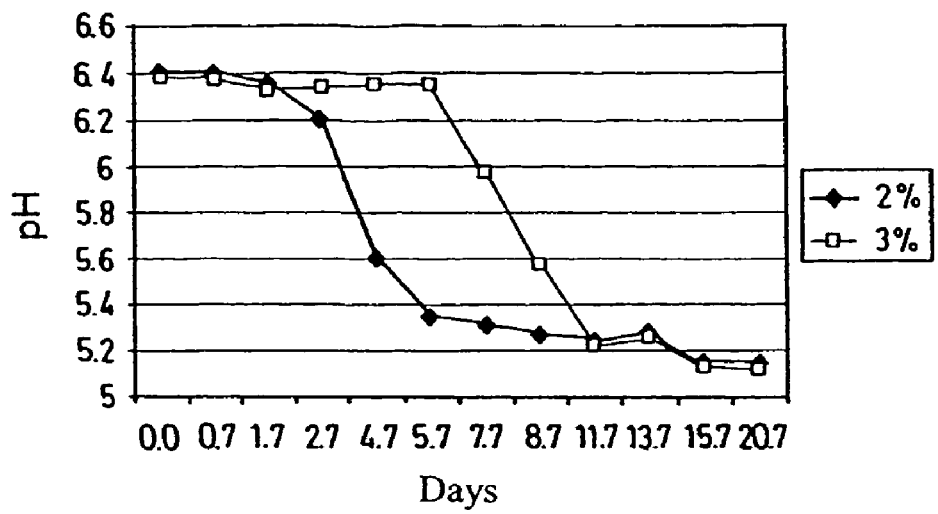
FIG. 7 shows the course of the pH as a function of the gelatin concentration.

Other parameters are capable of having an effect on the development of the microbial substance. For example, the quality and the quantity of texturing agent used in the indicator. For example, for a gelling agent, the greater the strength of the gel formed will be (because of the properties of the gelling agent or because of its concentration), the less quickly can the strain develop, which will slow down the kinetics of acidification of the medium. For example, for a given medium formulation, and for a given strain, the acidification of the medium is slower with 3% chicken gelatin than with 2% chicken gelatin (Bloom strength 200), as shown in FIG. 7 (the indicator, in this example, comprises a starter of $1 \times 10^6$ CFU per mL of the strain CRYO-CB002 with 2% and 3% chicken gelatin 200 with a starting pH of 6.4 and for preservation conditions of ⅓ of the time at +4° C. and ⅔ at +8° C.

The parameter $a_w$ is important for the rate of development of the microbial substance. $a_w$ is the water activity; it expresses the availability of water in a medium. It is important to make a distinction between unconfined, chemically unbound water (completely available to participate in reactions) and bound water (not available, in particular, for microorganisms). The $a_w$ is inversely proportional to the osmotic pressure of a compound. Thus, it is affected by the larger or smaller presence of moistening agents (e.g. NaCl (salts), glycerol, sorbitol, . . .) dissolved in water. The availability of the water present in a medium or in a substance intervenes in the growth of bacteria. The lowering of the $a_w$ slows down the enzyme activity; it increases the duration of the latency phase of the microorganisms and reduces their rate of growth. Thus, modifying the concentration of glycerol or of any other moistening agent to vary the value of $a_w$, as shown in Table 4 below, is beneficial and makes it possible to modify and control the growth times of the bacteria.

TABLE 4

| $A_w$ | Percentage of glycerol in the medium (in g) | Percentage of NaCl in the medium (in g) |
| --- | --- | --- |
| 0.995 | 0 | 0 |
| 0.990 | 3 | 1 |
| 0.985 | 6 | 2.5 |
| 0.980 | 10 | 3.5 |
| 0.975 | 13.5 | 4.5 |
| 0.970 | 15 | 5 |
| 0.960 | 20 | 6.5 |

$a_w$ corresponding to the percentage of NaCl and glycerol present in the medium.

Figure 8:
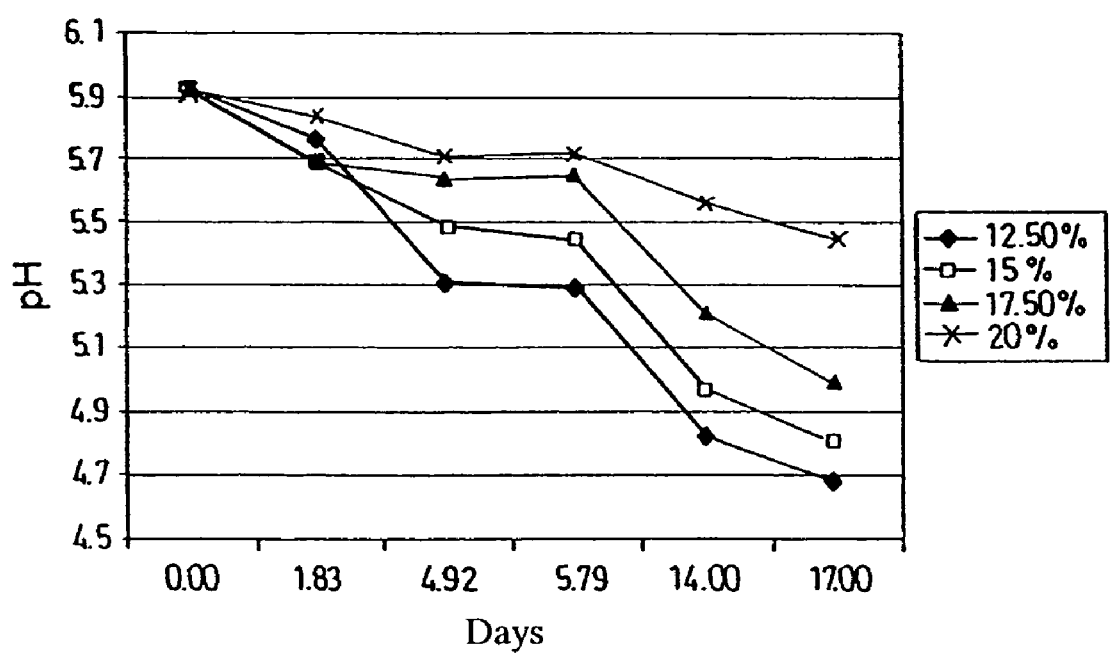
FIG. 8 shows the acidification of the medium by the strain CRYO-CB002 at 8° C. with different glycerol concentrations.

Generally, lowering the $a_w$ of the medium, on this side of the optimal $a_w$ value of a strain, slows down the kinetics of acidification of the medium. For example, the greater is the glycerol or NaCl concentration in the medium, the more slowed down the change in condition of the indicator will be (for a given indicator formulation). For example, at +8° C., with the strain CRYO-CB002, the acidification is slower if the medium contains 20% glycerol than if it contains 12.5% thereof, as shown in FIG. 8.

Finally, the starting pH of the medium is important for parameterizing the indicator.

On the one hand, the pH of the medium must be compatible with the development and the metabolic activity of the microbial substance. For example, for the strain CRYO-CB002, the pH must be in the range of 3.6 to 9.2. The pH of the medium has an effect on the rate of development of the microbial substance (for example, lactic acid bacteria) and therefore on its acidifying activity. The best microbial developments, and therefore the fastest acidification kinetics, are obtained at pH values close to the optimal growth pH of the selected strain (for example, pH 7.1 for the strain CRYO-CB002).

Figure 9A:
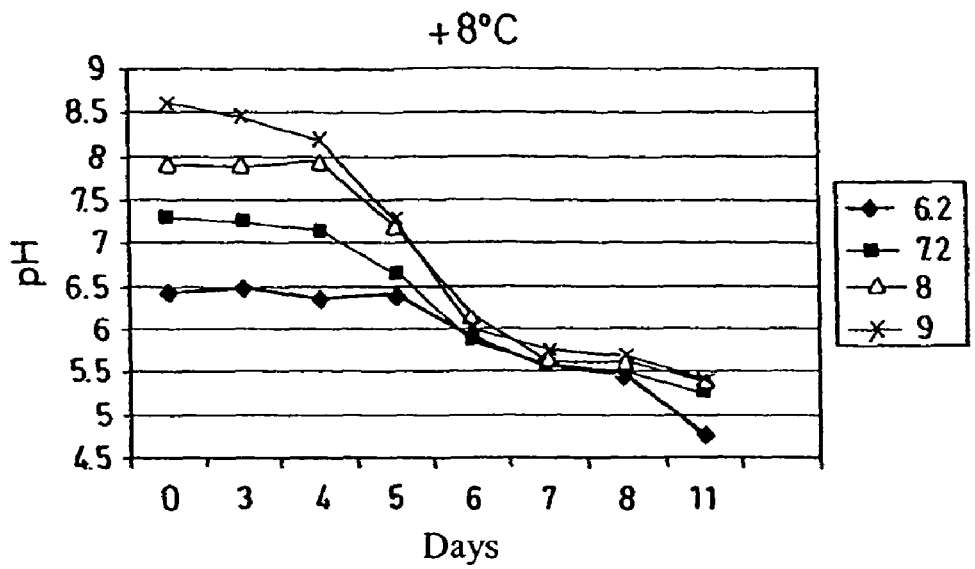
FIG. 9 shows the rate of acidification of the medium by the strain CRYO-CB002 as a function of the starting pH for two temperatures.
Figure 9B:
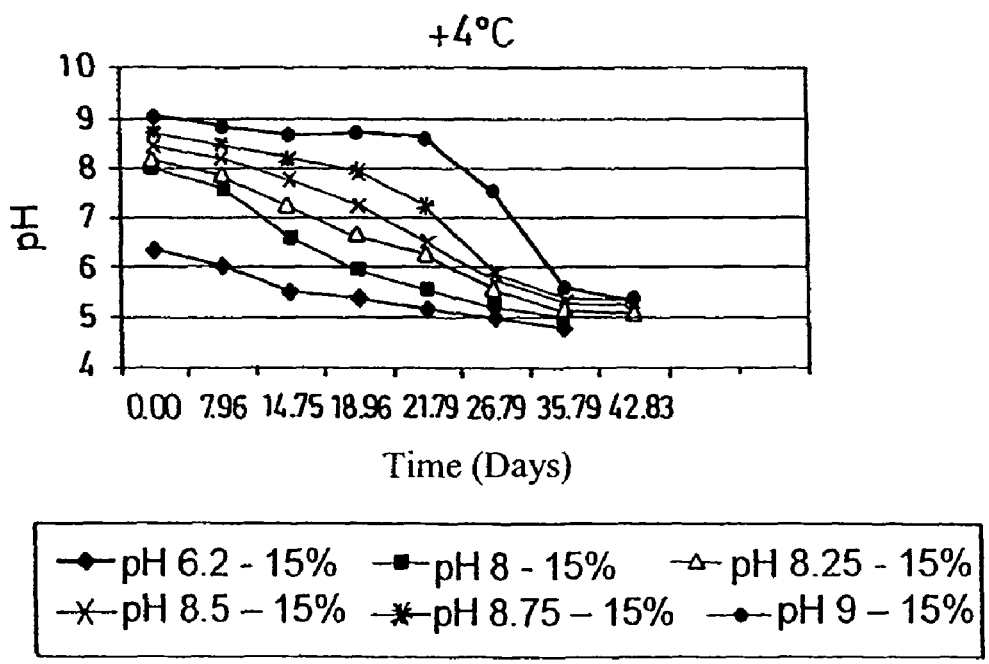

On the other hand, as the change in condition of the indicator results from the pH dropping below a threshold value, the further away the starting pH of the medium is from the threshold pH, the more time is required for the pH of the medium to decrease (thanks to the acidifying activity of the microbial substance) down to this threshold value. In other words, the higher the pH of the indicator will be (and higher than the optimal growth pH of the strain), the later will the change in condition of the indicator take place (for a given temperature). For example, the acidification of the medium by the strain CRYO-CB002 takes place later if the starting pH is 9 than if it is 6.2, as shown in FIG. 9-$a$ at +8° C. (the indicator comprises, in this example, 2.5% chicken gelatin 200 and a starter of $1\times10^5$ CFU per mL of the strain CRYO-CB002) and FIG. 9-$b$ at +4° C. (the indicator comprises, in this example, a starter of $1\times10^6$ CFU per mL of the strain CRYO-CB002 and 15% glycerol).

Finally, if the starting pH of the medium is buffered at a given pH (with a phosphate or Tris buffer, for example), the pH of the indicator will drop more slowly, which will delay the moment at which the developer or the developers will change condition. For example, at +8° C., for a 1% agar medium at pH 6.2; containing 2% mannitol; 15% glycerol; 5% sodium caseinate; 3% mixed indicator; inoculated at $1\times10^4$ CFU per mL with the strain CRYO-CB002, the precipitation time is 12 days when the starting pH is adjusted with HCl or NaOH, and the precipitation time is 17 days if a 0.1M phosphate buffer is used.

For the parameterization, we mentioned the principal elements entering into the manufacture of the indicator and having an effect on the rate of growth of the microbial substance as well as on the rate of acidification of the medium by the said microbial substance.

The rate of acidification of the medium will determine the time which is needed, at a given temperature, for the pH of the medium to reach the threshold value at which the developer or the developers will change condition (for example, a precipitation of casein or a color change of a color indicator).

In order to illustrate the data about the parameterization of the indicator and to provide the information needed for the good clarification of same, here are a series of formulation examples of the indicator as a function of the consume-by or optimal use-by dates in relation to different preservation temperatures.

For these examples, the inventors paid attention to validating the consume-by dates of perishable products as they were previously defined by the manufacturer under the conditions of the AFNOR standard NF V 01-003 by parameterizing the indicator on the said date as described in the first application, as summarized in Table 5.

TABLE 5

| Use-by date (opacification time of the indicator) | Temperature condition | Strain | Starter CFU/mL | Starting pH | Medium |
|---|---|---|---|---|---|
| 7 days | ⅓ +4° C.; ⅔ +8° C. | CRYO-CB002 | $1\times10^4$ | 6.2 | Glucose 2%<br>Agar 1%<br>Na+ caseinate 5% |
| 10 days | ⅓ +4° C.; ⅔ +8° C. | CRYO-CB002 | $1\times10^4$ | 6.2 | Glucose 2%<br>Glycerol 15%<br>Agar 1%<br>Na+ caseinate 5% |
| 20 days | ⅓ +4° C.; ⅔ +8° C. | CRYO-CB002 | $1\times10^4$ | 6.2 | Mannitol 2%<br>Glycerol 20%<br>Agar 1%<br>0.1M phosphate buffer<br>Na+ caseinate 5% |
| 11 days | ⅔ +4° C.; ⅓ +8° C. | CRYO-CB002 | $1\times10^4$ | 6.5 | Glucose 2%<br>Scleroglucan 1%<br>Na+ caseinate 10% |
| 13 days | +4° C. | CRYO-CB002 | $1\times10^4$ | 6.5 | Glucose 2%<br>Xanthan 0.25%<br>Na+ caseinate 10% |
| 10 days | ⅔ +4° C.; ⅓ +8° C. | CRYO-CB002 | $1\times10^7$ | | Glucose 2%<br>Porcine gelatin 310 1.6%<br>Na+ caseinate 10% |
| 9 days | +8° C. | CRYO-CB002 | $1\times10^5$ | 6.2 | Glucose 2%<br>Porcine gelatin 310 1.2%<br>Na+ caseinate 10% |
| 7 days | +8° C. | ATCC 10880 | $1\times10^5$ | 6.2 | Glucose 2%<br>Porcine gelatin 310 1.2%<br>Na+ caseinate 10% |
| 18 days | ⅔ +4° C.; ⅓ +8° C. | CRYO-CB002 | $1\times10^5$ | 6.2 | Glucose 2%<br>Porcine gelatin 310 1.2%<br>Na+ caseinate 10% |
| 13 days | ⅔ +4° C.; ⅓ +8° C. | ATCC 10880 | $1\times10^5$ | 6.2 | Glucose 2%<br>Porcine gelatin 310 1.2%<br>Na+ caseinate 10% |
| 21 days | +4° C. | CRYO-CB002 | $1\times10^5$ | 6.2 | Glucose 2%<br>Porcine gelatin 310 1.2%<br>Na+ caseinate 10% |

TABLE 5-continued

| Use-by date (opacification time of the indicator) | Temperature condition | Strain | Starter CFU/mL | Starting pH | Medium |
|---|---|---|---|---|---|
| 18 days | +4° C. | ATCC 10880 | $1 \times 10^5$ | 6.2 | Glucose 2%<br>Porcine gelatin 310 1.2%<br>Na+ caseinate 10% |
| 16 days | +4° C. | CIP 107633 | $1 \times 10^5$ | 6.4 | Glucose 2%<br>Porcine gelatin 310 5%<br>Na+ caseinate 10% |
| 8 days | +8° C. | CIP 107633 | $1 \times 10^5$ | 6.4 | Glucose 2%<br>Porcine gelatin 310 5%<br>Na+ caseinate 10% |
| 4 days | +15° C. | CIP 107633 | $1 \times 10^5$ | 6.4 | Glucose 2%<br>Porcine gelatin 310 5%<br>Na+ caseinate 10% |
| 2 days | +30° C. | CIP 107633 | $1 \times 10^5$ | 6.4 | Glucose 2%<br>Porcine gelatin 310 5%<br>Na+ caseinate 10% |
| 16 days | +8° C. | CRYO-CB002 | $1 \times 10^5$ | 6.4 | Glucose 2%<br>Porcine gelatin 310 5%<br>Na+ caseinate 10% |

The present invention is not limited to the embodiments described, and the person skilled in the art will recognize the existence of various embodiment variants, such as, for example, the use in the indicator of a selection of strains that are resistant to low temperatures to follow the course of a product that might undergo a freezing step, or even of a selection of specific strains at temperatures higher than those presented in this description, or even the use of a mixture of selected strains.

According to another of its aspects, the present invention pertains to a method for checking the real consume-by date of a perishable product, this consume-by date being reached when the product has been preserved for a certain period of time under recommended temperature conditions, a method according to which an indicator component comprising:

a microorganism having certain growth characteristics under recommended temperature conditions for the said product, these characteristics depending on the time and the temperature;

a culture medium for the microorganism, and a developer agent depending on the growth threshold of the microorganism, is combined with the product, so that the indicator provides an indication of a change in condition on the recommended use-by date when the product has been preserved under the recommended temperature conditions, or before this date or after this date, when the product has been preserved under worse or better temperature conditions, respectively.

In one embodiment, the microorganism is an acid-producing microorganism, and the developer agent is dependent on the pH of the medium.

In one embodiment, the developer agent is casein, which forms a precipitate when the pH of the medium drops below a predetermined value.

The developer agent may be a pH-dependent color indicator.

In one embodiment, the microorganism is a population of lactic acid bacteria, preferably of the genus *Lactobacillus, Enterococcus, Carnobacterium* or *Leuconostoc.*

In this case, the indicator component may be included in a film, at least one face of which comprises a zone making it possible to observe the signal produced by the developer agent, comprising a predetermined quantity of acidifying microorganism in an appropriate culture medium, a developer agent. The label may also comprises a plurality of internal compartments, for example, capsules, making it possible to separate one or more constituents of the component from the others for a certain period of time, the walls of the said compartments being able to be broken by any suitable means, for example, by pressing on the label.

In one embodiment, the perishable product is a food or pharmaceutical product. This perishable product is, for example, a food product intended to be preserved at a temperature of about +4° C., and in which the indicator component comprises a microorganism capable of growth at a temperature lower than or equal to +4° C.

The present invention also pertains to a biological indicator component characterized in that it comprises, in a packaging, a population of acidifying microorganisms with growth characteristics depending on the time and the temperature, a culture medium for the microorganism, a developer agent depending on the pH of the medium, and a texturing agent, at least one surface zone of the packaging making it possible to observe the signal produced by the developer agent.

In one embodiment, the microorganisms are present in an isolated compartment, for example, capsules.

In one embodiment, the constituents are selected to make possible the production of a signal by the developer agent after preservation of the component for a predefined period of time at a predefined temperature.

In one embodiment, the developer agent is casein, which forms a precipitate when the pH of the medium drops below a predetermined value.

In one embodiment, the developer agent is a pH-dependent color indicator.

In one embodiment, the microorganism is a population of lactic acid bacteria of the genus *Lactobacillus, Enterococcus, Carnobacterium* or *Leuconostoc.*

In one embodiment, the microorganism is a population of lactic acid bacteria capable of growing at temperatures lower than +8° C., preferably lower than +6° C., and more preferably at a temperature of 4° C. or lower.

In one embodiment, the microorganism is a population of lactic acid bacteria capable of growing at temperatures ranging from −4° C. to +50° C.

In one embodiment, the microorganism may be frozen and thawed.

In one embodiment, the microorganism is selected from among the lactic acid bacteria *Carnobacterium piscicola,* or *Lactobacillus fuchuensis,* or *Leuconostoc mesenteroides.*

In one embodiment, the culture medium comprises nutrients necessary for the survival and the development of the microorganisms, as well as the acidifying function.

The present invention also pertains to a method of preparation of a biological indicator component defined above comprising the obtaining of a population of acidifying microorganisms having growth characteristics depending on the time and the temperature and the packaging of these microorganisms in an appropriate culture medium in the presence of a developer agent depending on the pH of the medium and, if necessary, a texturing agent, in a packaging, at least one surface zone of which makes it possible to observe the signal produced by the developer agent.

In one embodiment, some constituents of the indicator are placed in separate compartments, whose walls can be broken.

The present invention also pertains to the unit formed by a perishable product and an indicator component as defined above, which is combined with this product, in particular by means of opposition.

In one embodiment, the indicator component is affixed by adhesive means.

In one embodiment, the indicator component comprises a plurality of compartments and is activated after, or at the time of affixing, by breaking the walls of the compartments.

In one embodiment, the perishable product is a food or pharmaceutical product.

The invention claimed is:

1. Method for determining whether or not a heat-sensitive product is in a condition to be used or consumed, the heat-sensitive product being intended to be preserved below a predetermined temperature limit under predetermined temperature conditions and for a period of time which limit its degradation, comprising the steps of:
combining an indicator comprising a microbial substance selected from the group consisting of *Canobacterium piscicola, Lactobacillus fuchuensis* and *Leuconostoc mesenteroides* with the heat-sensitive product, the indicator providing a signal indicating that the heat-sensitive product can be used or consumed, and after the expiration of a preservation period of time, the indicator further providing a signal indicating a change in the condition of using or consuming the heat-sensitive product for a period of time depending on the preservation conditions of the product,
the indicator being activated as soon as it is combined with the heat-sensitive product and providing information enabling the heat-sensitive product to be used or consumed for a longer period of time if the heat-sensitive product has been preserved under conditions better than standard or recommended temperature conditions, without exceeding the predetermined temperature limit or without breaking a cold chain associated with the heat-sensitive product.

2. Method in accordance with claim 1, wherein the indicator further provides information enabling the heat-sensitive product to be used or consumed for a shorter period of time if the product has been preserved under temperature conditions worse than the standard or recommended temperature conditions.

3. Method in accordance with claim 1, wherein the indicator includes an acidifying microbial substance, and the signal is produced using a developer, the developer indicating a change in condition of the heat-sensitive product when pH of a medium in which the microbial substance is located, drops below a predetermined value.

4. Method in accordance with claim 3, in wherein the developer forms a precipitate when the pH drops below the predetermined value.

5. Method in accordance with claim 4, wherein the developer comprises casein.

6. Method in accordance with claim 3, wherein the developer further comprises at least one color indicator.

7. Method in accordance with claim 6, wherein the color indicator is selected from the group consisting of: Alizarine, alizarine sodium sulfonate, alizarine red, benzopurpurine, benzoyl auramine G, benzoylethyl auramine, resorcinol blue, bromochlorophenol blue, bromocresol green, bromophenol blue, carmine acid, 2,4-dinitrophenol, 4-(4-dimethylamino-1-naphthylazo)-3-methoxybenzene sulfonic acid, α-dinitrophenol, β-dinitrophenol, γ-dinitrophenol, disodium 4,4-bis(o-tolytriazeno)-2,2'-stilbene disulfonate, disodium 4,4-bis(p-dimethylaminophenylazo)-2,2'-stilbene disulfonate, 4-(p-ethoxyphenylazo)-m-phenylene-diamine monohydrochloride, ethyl red, ethyl orange, hexamethoxy red, hydroquinol sulfonaphthalein, lacmoid, iodeosin, lasmoid, N,N-dimethyl-p-(m-tolylazo)aniline, 4'-methoxy-2,4-diaminoazobenzene, methyl red, methyl red alphazurin, α-naphthylamine, α-naphthylaminoazobenzene, naphthyl red, oxime blue, 4'-oxy-3'-methyl-2,4-diaminoazobenzene, 4'-oxy-2,4,-diaminoazobenzene, 4-phenylazo-1-naphthylamine, parafuchsin-hexa-acetic acid, paranitrophenol, p-ethoxychrysoidine, p-sulfo-o-methoxybenzeneazodimethyl-α-naphthylamine, Congo red, violet red, resazurin, naphthyl red, tetrabromocresol, tetraiodophenol sulfophthalein, aurin acid, dithiozone, chromium blue, bromocresol purple, indigo carmine, cacotheline, calceine, eosin extra, eriochromocyanine, thiazole yellow, eriochromium black T, α-nitro-β-naphthol, orange III, methyl red, rhodamine B, potassium rhodazonate, thymolsulfophthalein, rhodium chloride, trihydroxy-2,6,7-phenyl-9 isoxanthene, thorium oxide, xylene orange tetrasodium salt, anthocyanes, phenolphthalein, benzopurpurine 4B, benzopurpurine B, alpha naphthyl red hydrochloride, litmus, methyl red, mixed indicator, and lacmoid.

8. Method in accordance with claim 1, further comprising the step of modifying the indicator to the heat-sensitive product using at least one parameters selected from the group consisting of: the microbial substance, the quantity of the microbial substance, nutrients for the microbial substance, a quantity of the nutrients, elements needed for production of acid by the microbial substance and a quantity of these elements, a texturing agent of the medium in which the microbial substance is located and a quantity of this texturing agent, starting pH of the medium, $a_w$ (water activity) of the medium, the developer used for measuring the drop in the pH and the quantity of this developer, and parameters used in determining the pH at which this developer changes condition.

9. Method in accordance with claim 8, wherein the parameters are selected so that the signal indicating the change in condition takes place after a predetermined period of time when the heat-sensitive product is under the predetermined standard or recommended temperature conditions.

10. Method in accordance with claim 8, wherein the parameters are selected so that the signal indicating the change in condition of the heat-sensitive product appears when the heat-sensitive product can no longer be consumed.

11. Method in accordance with claim 9, in which, under the predetermined standard or recommended temperature conditions, the parameters of the indicator are selected so that the signal indicating the change in condition of the heat-sensitive product takes place after a certain period of time, the period of time being increased by modifying one of these parameters to move away from optimal values for the acidification by the microbial substance.

12. Method in accordance with claim 8, wherein the nutrients further comprise at least one of a carbon source, a nitrogen source, inorganic salts, vitamins or trace elements.

13. Method in accordance with claim 12, in which the carbon source is selected from sugars forming the group consisting of:

Glycerol, erythritol, D-arabinose, L-arabinose, ribose, D-xylose, L-xylose, adonitol, β-methylxyloside, galactose, D-glucose, D-fructose, D-mannose, L-sorbose, rhamnose, dulcitol, inositol, mannitol, sorbitol, α-methyl-D-mannoside, α-methyl-D-glucoside, N-acetylglucosamine, amygdalin, arbutin, esculin, salicin, cellobiose, maltose, lactose, melibiose, sucrose, trehalose, inulin, melezitose, D-raffinose, starch, glycogen, xylitol, β-gentiobiose, D-turanose, D-lyxose, D-tagatose, D-fucose, L-fucose, D-arabitol, L-arabitol, gluconate, 2-keto-gluconate, and 5-keto-gluconate.

14. Method in accordance with claim 8, further comprising a texturing agent selected from: agar, agarose, gelatin, xanthan, scleroglucan, and guar gum.

15. Method in accordance with claim 1, wherein the indicator is inactivated when it is not combined with the heat-sensitive product and is activated when it is combined with the heat-sensitive product.

16. Method in accordance with claim 15, wherein indicator inactivation is carried out by one of the following physical actions: freezing, microencapsulation of the microbial substance and/or nutrients, and dividing the heat-sensitive product and the indicator into compartments.

17. Method in accordance with claim 15 or 16, wherein the indicator is activated by a physical action selected from: pressure variation, temperature variation, and variation in wavelength of exposure to radiation.

18. Method in accordance with claim 1, wherein the microbial substance remains operable when frozen and thawed.

19. Method in accordance with claim 1 wherein the heat-sensitive product is selected from a group consisting of: heat-sensitive food products, heat-sensitive biological products and heat-sensitive pharmaceutical products.

20. Method in accordance with claim 1 further comprising heat-sensitive food products wherein the indicator is parameterized so that the appearance of the signal indicating a change in condition in the heat-sensitive food products is delayed when the preservation temperature of the product is close to an optimal preservation temperature.

21. Method in accordance with claim 1 further comprising a heat-sensitive food product intended to be preserved at temperatures ranging from about 0° C. to about +4° C., and wherein the indicator comprises a microbial substance having an acidifying activity at temperatures lower than or equal to about +4° C.

22. Device for determining whether or not a heat-sensitive product is in a condition to be used or consumed, the heat-sensitive product being intended to be preserved below a predetermined temperature limit under predetermined temperature conditions and for a period of time which limit its degradation, the device comprising: at least one indicator comprising at least one microbial substance selected from the group consisting of *Canobacterium piscicola, Lactobacillus fuchuensis* and *Leuconostoc mesenteroides* configured to be combined with the heat-sensitive product, the indicator providing a signal indicating that the heat-sensitive product can be used or consumed, and after the expiration of a preservation period of time, the indicator further providing a signal indicating a change in the condition of the heat-sensitive product for a period of time depending on the preservation conditions of the heat-sensitive product, the indicator being configured to be activated as soon as it is combined with the product and further providing information enabling the heat-sensitive product to be used or consumed for a longer period of time if the heat-sensitive product has been preserved under conditions better than standard or recommended temperature conditions without exceeding the predetermined temperature limit or without breaking a cold chain.

23. Device in accordance with claim 22, wherein the indicator further provides information enabling the heat-sensitive product to be used or consumed for a shorter period of time if the heat-sensitive product has been preserved under conditions worse than the standard or recommended conditions.

24. Device in accordance with claim 22, wherein the indicator includes an acidifying microbial substance and the device further comprises a developer for providing a signal indicating the change in condition of the heat-sensitive product when a pH of a medium in which the microbial substance is located, drops below a predetermined value.

25. Device in accordance with claim 24, wherein the developer forms a precipitate when the pH drops below the predetermined value.

26. Device in accordance with claim 25, wherein the developer comprises casein.

27. Device in accordance with claim 24, wherein the developer further comprises at least one color indicator.

28. Device in accordance with claim 27, wherein the color indicator is selected from the group consisting of: Alizarine, alizarine sodium sulfonate, alizarine red, benzopurpurine, benzoyl auramine G, benzoylethyl auramine, resorcinol blue, bromochlorophenol blue, bromocresol green, bromophenol blue, carmine acid, 2,4-dinitrophenol, 4-(4-dimethylamino-1-naphthylazo)-3-methoxybenzene sulfonic acid, α-dinitrophenol, β-dinitrophenol, γ-dinitrophenol, disodium 4,4-bis(o-tolytriazeno)-2,2'-stilbene disulfonate, disodium 4,4-bis(p-dimethylaminophenylazo)-2,2'-stilbene disulfonate, 4-(p-ethoxyphenylazo)-m-phenylene-diamine monohydrochloride, ethyl red, ethyl orange, hexamethoxy red, hydroquinol sulfonaphthalein, lacmoid, iodeosin, lasmoid, N,N-dimethyl-p-(m-tolylazo)aniline, 4'-methoxy-2.4-diaminoazobenzene, methyl red, methyl red alphazurin, α-naphthylamine, α-naphthylaminoazobenzene, naphthyl red, oxime blue, 4'-oxy-3'-methyl-2.4-diaminoazobenzene, 4'-oxy-2.4-diaminoazobenzene, 4-phenylazo-1-naphthylamine, parafuchsin-hexa-acetic acid, paranitrophenol, p-ethoxychrysoidine, p-sulfo-o-methoxybenzeneazodimethyl-α-naphthylamine, Congo red, violet red, resazurin, naphthyl red, tetrabromocresol, tetraiodophenol sulfophthalein, aurin acid, dithiozone, chromium blue, bromocresol purple, indigo carmine, cacotheline, calceine, eosin extra, eriochromocyanine, thiazole yellow, eriochromium black T, α-nitro-β-naphthol, orange III, methyl red, rhodamine B, potassium rhodazonate, thymolsulfophthalein, rhodium chloride, trihydroxy-2,6,7-phenyl-9 isoxanthene, thorium oxide, xylene orange tetrasodium salt, anthocyanes, phenolphthalein, benzopurpurine 4B, benzopurpurine B, alpha naphthyl red hydrochloride, litmus, methyl red, mixed indicator, and lacmoid.

29. Device in accordance with claim 22 wherein at least one of the parameters of the indicator is modified in the heat-sensitive product, the parameters selected from the group consisting of: the microbial substance, the quantity of the microbial substance, nutrients for the microbial substance, a quantity of the nutrients, elements needed for the production of acid by the microbial substance and a quantity of these elements, a texturing agent of the medium in which the microbial substance is located and the quantity of this texturing agent, a starting pH of the medium, $a_w$ (water activity) of the medium, the developer used for measuring the drop in the pH and a quantity of this developer, and parameters used in determining the pH at which this developer changes condition.

30. Device in accordance with claim 29, wherein the indicator provides a signal indicating the change in condition of the heat-sensitive product that takes place after a predetermined period of time when the heat-sensitive product is preserved under the predetermined standard or recommended temperature conditions.

31. Device in accordance with claim 29, further comprising an indicator providing a signal indicating the change in condition of the heat-sensitive product appears when the heat-sensitive product can no longer be consumed or used.

32. Device in accordance with claim 29, wherein the nutrients further comprise at least one of a carbon source, and a nitrogen source, inorganic salts, vitamins or trace elements.

33. Device in accordance with claim 32, wherein the carbon source is selected from sugars consisting of: Glycerol, erythritol, D-arabinose, L-arabinose, ribose, D-xylose, L-xylose, adonitol, β-methylxyloside, galactose, D-glucose, D-fructose, D-mannose, L-sorbose, rhamnose, dulcitol, inositol, mannitol, sorbitol, α-methyl-D-mannoside, α-methyl-D-glucoside, N-acetyl-glucosamine, amygdalin, arbutin, esculin, salicin, cellobiose, maltose, lactose, melibiose, sucrose, trehalose, inulin, melezitose, D-raffinose, starch, glycogen, xylitol, β-gentiobiose, D-turanose, D-lyxose, D-tagatose, D-fucose, L-fucose, D-arabitol, L-arabitol, gluconate, 2-keto-gluconate, and 5-keto-gluconate.

34. Device in accordance with claim 29, further comprising a texturing agent is selected from the group consisting of: agar, agarose, gelatin, xanthan, scleroglucan, and guar gum.

35. Device in accordance with claim 23, wherein the indicator is inactivated when it is not combined with the heat-sensitive product and is activated when it is combined with the heat-sensitive product.

36. Device in accordance with claim 35, wherein indicator inactivation is carried out by one of the following physical actions: freezing, microencapsulation of the microbial substance and/or nutrients, and dividing the heat-sensitive product and the indicator into compartments.

37. Device in accordance with claim 35, wherein the indicator is activated by a physical action selected from: pressure variation, temperature variation, and variation in wavelength of exposure to radiation.

38. Device in accordance with claim 22, wherein the microbial substance remains operable when frozen and thawed.

39. Device in accordance with claim 23, wherein the indicator further comprises a label or a self-adhesive label.

40. Device in accordance with claim 39, wherein the indicator comprises at least one face, one zone of which is used for observing the signal produced by the developer.

41. Device in accordance with claim 39 or 40, wherein the label further comprises a plurality of internal compartments for separating one or more constituents of the indicator from components of the indicator for a certain period of time, the walls of the compartments being able to be broken by any suitable means, including by pressing on the label.

* * * * *